(12) United States Patent
Gozani et al.

(10) Patent No.: US 11,730,959 B2
(45) Date of Patent: *Aug. 22, 2023

(54) APPARATUS AND METHOD FOR BUTTON-FREE CONTROL OF A WEARABLE TRANSCUTANEOUS ELECTRICAL NERVE STIMULATOR USING INTERACTIVE GESTURES AND OTHER MEANS

(71) Applicant: Neurometrix, Inc., Woburn, MA (US)

(72) Inventors: Shai N. Gozani, Newton, MA (US); Xuan Kong, Acton, MA (US); Thomas C. Ferree, Waltham, MA (US)

(73) Assignee: Neurometrix, Inc., Woburn, MA (US)

( * ) Notice: Subject to any disclaimer, the term of this patent is extended or adjusted under 35 U.S.C. 154(b) by 53 days.

This patent is subject to a terminal disclaimer.

(21) Appl. No.: 17/196,176

(22) Filed: Mar. 9, 2021

(65) Prior Publication Data
US 2021/0260374 A1 Aug. 26, 2021

Related U.S. Application Data

(63) Continuation of application No. 16/010,974, filed on Jun. 18, 2018, now Pat. No. 10,940,311, which is a (Continued)

(51) Int. Cl.
*A61N 1/36* (2006.01)
*A61B 5/11* (2006.01)
(Continued)

(52) U.S. Cl.
CPC ........ *A61N 1/36021* (2013.01); *A61B 5/1118* (2013.01); *A61B 5/1123* (2013.01);
(Continued)

(58) Field of Classification Search
CPC .................. A61N 1/36021; A61N 1/36031
(Continued)

(56) References Cited

U.S. PATENT DOCUMENTS

| 1,741,962 A | 12/1929 | Theodoropulos |
| 4,290,431 A | 9/1981 | Herbert et al. |

(Continued)

FOREIGN PATENT DOCUMENTS

| CN | 1665563 | 9/2005 |
| CN | 1919139 | 2/2007 |

(Continued)

OTHER PUBLICATIONS

Amazon, "Quell 2.0 Wearable Pain Relief Technology", Sep. 15, 2018.http://www.amazon/com/Quell-Wearable-Pain-Relief-Technology/dp/B07DHW2MJJ/ref=cm_cr_arp_d_product_top?ie=UTF8. Shown on p. 1. (Year: 2018).

(Continued)

*Primary Examiner* — Carl H Layno
*Assistant Examiner* — Manolis Pahakis
(74) *Attorney, Agent, or Firm* — Pandiscio & Pandiscio

(57) ABSTRACT

Apparatus for transcutaneous electrical nerve stimulation in a user, the apparatus comprising: a stimulator for electrically stimulating at least one nerve, a stimulator housing, a monitor for monitoring transient motion of the stimulator housing, an analyzer for analyzing transient motion monitored by the monitor for determining whether transient motion of the stimulator housing has occurred, and a controller for automatically transitioning at least one of the stimulator, the monitor, and the analyzer between a standby mode and a power save mode, wherein the power save mode supports a subset of the functionality of the stimulator and the monitor which is available in the standby mode so as to conserve battery power in the power save mode.

34 Claims, 14 Drawing Sheets

Related U.S. Application Data continuation-in-part of application No. 15/824,351, filed on Nov. 28, 2017, now Pat. No. 10,130,810, which is a continuation of application No. 14/269,887, filed on May 5, 2014, now Pat. No. 9,827,420, which is a continuation-in-part of application No. 14/253,628, filed on Apr. 15, 2014, now Pat. No. 10,279,179, and a continuation-in-part of application No. 14/230,648, filed on Mar. 31, 2014, now Pat. No. 9,474,898.

(60) Provisional application No. 62/524,195, filed on Jun. 23, 2017, provisional application No. 61/858,150, filed on Jul. 25, 2013, provisional application No. 61/819,159, filed on May 3, 2013, provisional application No. 61/811,864, filed on Apr. 15, 2013, provisional application No. 61/806,481, filed on Mar. 29, 2013.

(51) Int. Cl.

| | |
|---|---|
| *G06F 1/3231* | (2019.01) |
| *G06F 3/0346* | (2013.01) |
| *G06F 1/16* | (2006.01) |
| *A61B 5/00* | (2006.01) |
| *A61N 1/04* | (2006.01) |
| *A61N 1/08* | (2006.01) |
| *G06F 3/01* | (2006.01) |

(52) U.S. Cl.
CPC .......... *A61B 5/7475* (2013.01); *A61N 1/0456* (2013.01); *A61N 1/0492* (2013.01); *A61N 1/08* (2013.01); *A61N 1/36031* (2017.08); *G06F 1/163* (2013.01); *G06F 1/3231* (2013.01); *G06F 3/015* (2013.01); *G06F 3/017* (2013.01); *G06F 3/0346* (2013.01); *A61B 5/11* (2013.01); *A61B 5/681* (2013.01); *A61B 5/6828* (2013.01); *A61B 5/7455* (2013.01); *A61B 2560/0276* (2013.01); *A61B 2562/0219* (2013.01); *A61N 2001/083* (2013.01)

(58) Field of Classification Search
USPC .......................................................... 607/46
See application file for complete search history.

(56) References Cited

U.S. PATENT DOCUMENTS

| | | | |
|---|---|---|---|
| D263,869 S | 4/1982 | Sumiyasu | |
| 4,503,863 A | 3/1985 | Katims | |
| 4,605,010 A | 8/1986 | McEwen | |
| 4,738,250 A | 4/1988 | Fulkerson et al. | |
| 4,777,711 A * | 10/1988 | Forkner | H01R 43/28 414/745.9 |
| 4,926,863 A * | 5/1990 | Alt | A61N 1/36542 607/18 |
| 4,989,605 A | 2/1991 | Rossen | |
| 5,048,523 A | 9/1991 | Yamasawa et al. | |
| 5,063,929 A * | 11/1991 | Bartelt | A61N 1/36021 607/66 |
| D323,561 S | 1/1992 | Bartelt et al. | |
| 5,121,747 A | 6/1992 | Andrews | |
| 5,169,384 A | 12/1992 | Bosniak et al. | |
| D342,571 S | 12/1993 | Givens, Sr. | |
| D346,029 S | 4/1994 | Shalvi | |
| 5,350,414 A | 9/1994 | Kolen | |
| 5,429,589 A | 7/1995 | Cartmell et al. | |
| 5,479,939 A | 1/1996 | Ogino | |
| 5,487,759 A | 1/1996 | Bastyr et al. | |
| 5,562,718 A | 10/1996 | Palermo | |
| 5,806,522 A | 9/1998 | Katims | |
| D411,887 S | 7/1999 | Agarwala | |
| 5,948,000 A | 9/1999 | Larsen et al. | |
| 5,954,758 A * | 9/1999 | Peckham | A61N 1/36003 607/48 |
| 6,033,370 A * | 3/2000 | Reinbold | A61B 5/6805 600/595 |
| 6,099,488 A | 8/2000 | Hung | |
| 6,132,387 A | 10/2000 | Gozani et al. | |
| 6,141,587 A | 10/2000 | Mower | |
| 6,148,233 A * | 11/2000 | Owen | A61N 1/0476 607/5 |
| 6,161,044 A | 12/2000 | Silverstone | |
| D443,362 S | 6/2001 | Storp | |
| 6,266,558 B1 | 7/2001 | Gozani et al. | |
| D450,313 S | 11/2001 | Koinuma | |
| 6,430,450 B1 | 8/2002 | Bach-y-Rita et al. | |
| D462,772 S | 9/2002 | Lamping et al. | |
| 6,456,884 B1 | 9/2002 | Kenney | |
| 6,611,789 B1 | 8/2003 | Darley | |
| 6,662,051 B1 | 12/2003 | Eraker et al. | |
| D484,984 S | 1/2004 | Takizawa et al. | |
| D534,871 S | 1/2007 | Larsen | |
| D541,042 S | 4/2007 | Andre et al. | |
| D547,454 S | 7/2007 | Hsieh | |
| D566,383 S | 4/2008 | Harris et al. | |
| D584,414 S | 1/2009 | Lash et al. | |
| D592,200 S | 5/2009 | Liu | |
| D598,556 S | 8/2009 | Chen | |
| D600,352 S | 9/2009 | Cryan | |
| D607,198 S | 1/2010 | Andre et al. | |
| D609,353 S | 2/2010 | Cryan | |
| 7,668,598 B2 | 2/2010 | Herregraven et al. | |
| D611,611 S | 3/2010 | Sachi et al. | |
| D615,526 S | 5/2010 | Andre et al. | |
| 7,720,548 B2 | 5/2010 | King | |
| 7,725,193 B1 | 5/2010 | Chu | |
| 7,787,946 B2 | 8/2010 | Stahmann et al. | |
| D625,016 S | 10/2010 | Potts et al. | |
| D625,829 S | 10/2010 | Arbesman et al. | |
| D629,115 S | 12/2010 | Robertson | |
| 7,887,493 B2 | 2/2011 | Stahmann et al. | |
| D636,881 S | 4/2011 | Clemens et al. | |
| D637,988 S | 5/2011 | Jinkinson | |
| 8,108,049 B2 | 1/2012 | King | |
| 8,121,702 B2 | 2/2012 | King | |
| 8,131,374 B2 | 3/2012 | Moore et al. | |
| D658,302 S | 4/2012 | Nixon | |
| 8,284,070 B2 | 10/2012 | Chaudhari et al. | |
| D677,792 S | 3/2013 | Vandiver | |
| D680,735 S | 4/2013 | Itabashi et al. | |
| 8,421,642 B1 | 4/2013 | McIntosh et al. | |
| D687,951 S | 8/2013 | Della Torre et al. | |
| D688,707 S | 8/2013 | Vincent et al. | |
| D704,848 S | 5/2014 | Thomas et al. | |
| D705,428 S | 5/2014 | Cheney et al. | |
| D712,045 S | 8/2014 | Thornton | |
| D712,052 S | 8/2014 | Thomas et al. | |
| D713,049 S | 9/2014 | Shah | |
| 8,825,175 B2 | 9/2014 | King | |
| 8,849,407 B1 | 9/2014 | Danilov et al. | |
| D716,457 S | 10/2014 | Brefka et al. | |
| 8,862,238 B2 * | 10/2014 | Rahimi | A61N 1/36021 607/46 |
| D716,963 S | 11/2014 | Yosef et al. | |
| 8,948,876 B2 | 2/2015 | Gozani et al. | |
| D732,682 S | 6/2015 | Porat | |
| D735,873 S | 8/2015 | Brefka et al. | |
| 9,168,375 B2 | 10/2015 | Rahimi et al. | |
| D744,661 S | 12/2015 | Rizzi | |
| D745,975 S | 12/2015 | Igaue et al. | |
| D750,263 S | 2/2016 | Shigeno et al. | |
| D750,798 S | 3/2016 | Yosef et al. | |
| 9,282,287 B1 | 3/2016 | Marsh | |
| 9,282,897 B2 | 3/2016 | Ross, Jr. et al. | |
| D754,355 S | 4/2016 | Ganapathy et al. | |
| D754,973 S | 5/2016 | Danze et al. | |
| D757,292 S | 5/2016 | Chen | |
| D758,605 S | 6/2016 | Chen | |

(56) References Cited

U.S. PATENT DOCUMENTS

| | | |
|---|---|---|
| D758,606 S | 6/2016 | Chen |
| D759,262 S | 6/2016 | Chen |
| D759,263 S | 6/2016 | Chen |
| D759,958 S | 6/2016 | Requa |
| D762,628 S | 8/2016 | Yoon et al. |
| D762,872 S | 8/2016 | Chen |
| D767,775 S | 9/2016 | Gilmer et al. |
| 9,452,287 B2 | 9/2016 | Rosenbluth et al. |
| 9,474,898 B2 | 10/2016 | Gozani et al. |
| D774,654 S | 12/2016 | Anderson |
| D775,361 S | 12/2016 | Vosch et al. |
| D778,453 S | 2/2017 | Knaus et al. |
| D779,677 S | 2/2017 | Chen |
| 9,561,397 B2 | 2/2017 | Zaki |
| D784,544 S | 4/2017 | Dudkiewicz et al. |
| D784,546 S | 4/2017 | Gordon |
| D784,946 S | 4/2017 | Jun et al. |
| D788,056 S | 5/2017 | Choi et al. |
| 9,656,070 B2 | 5/2017 | Gozani et al. |
| D789,546 S | 6/2017 | Matfus et al. |
| D789,547 S | 6/2017 | Matfus et al. |
| D791,333 S | 7/2017 | Wilson |
| D792,363 S | 7/2017 | Kim et al. |
| 9,700,724 B2 | 7/2017 | Liu et al. |
| D794,331 S | 8/2017 | Grote |
| 9,731,126 B2 | 8/2017 | Ferree et al. |
| D798,170 S | 9/2017 | Toth et al. |
| D801,542 S | 10/2017 | Anderson |
| D802,780 S | 11/2017 | Hsu |
| 9,827,420 B2 | 11/2017 | Ferree et al. |
| D806,669 S | 1/2018 | Kangasmaa et al. |
| D810,311 S | 2/2018 | Chen |
| D810,843 S | 2/2018 | Karvandi |
| D810,952 S | 2/2018 | Hsu |
| D811,729 S | 3/2018 | Bysshe |
| D813,405 S | 3/2018 | Ho |
| D813,407 S | 3/2018 | Chen |
| D813,408 S | 3/2018 | Chen |
| D821,592 S | 6/2018 | Pham et al. |
| D828,569 S | 9/2018 | Mercuro |
| D829,182 S | 9/2018 | Li |
| 10,076,662 B2 * | 9/2018 | Tuan ................. A61N 1/36021 |
| D830,565 S | 10/2018 | Xu |
| D831,017 S | 10/2018 | Choe et al. |
| D831,221 S | 10/2018 | Smith |
| D831,335 S | 10/2018 | Crease |
| D832,230 S | 10/2018 | Lee et al. |
| D834,719 S | 11/2018 | Theriot et al. |
| D836,788 S | 12/2018 | Peng |
| 10,154,922 B1 * | 12/2018 | Perez ................. A61N 1/36034 |
| D837,394 S | 1/2019 | Cryan et al. |
| 10,279,179 B2 | 5/2019 | Gozani et al. |
| 10,335,595 B2 | 7/2019 | Ferree et al. |
| D857,910 S | 8/2019 | Cryan et al. |
| D861,903 S | 10/2019 | Cryan et al. |
| D861,904 S | 10/2019 | Ho |
| D862,716 S | 10/2019 | Cryan et al. |
| D865,986 S | 11/2019 | Cryan et al. |
| D879,983 S | 3/2020 | Wang |
| 10,940,311 B2 * | 3/2021 | Gozani ................. A61N 1/36031 |
| 11,247,040 B2 | 2/2022 | Ferree et al. |
| 2002/0010497 A1 | 1/2002 | Merfeld et al. |
| 2003/0023192 A1 | 1/2003 | Foxlin |
| 2003/0074037 A1 | 4/2003 | Moore et al. |
| 2003/0114892 A1 | 6/2003 | Nathan et al. |
| 2003/0208246 A1 | 11/2003 | Kotlik et al. |
| 2004/0049241 A1 | 3/2004 | Campos |
| 2004/0122483 A1 * | 6/2004 | Nathan ................. A61N 1/36003 607/49 |
| 2004/0173220 A1 * | 9/2004 | Harry ................. A61N 1/32 128/892 |
| 2005/0059903 A1 | 3/2005 | Izumi |
| 2005/0080463 A1 | 4/2005 | Stahmann et al. |
| 2005/0097970 A1 | 5/2005 | Nurse |
| 2005/0131317 A1 | 6/2005 | Oddsson et al. |
| 2005/0234525 A1 | 10/2005 | Phillips |
| 2005/0283204 A1 | 12/2005 | Buhlmann et al. |
| 2006/0052788 A1 | 3/2006 | Thelen et al. |
| 2006/0064037 A1 * | 3/2006 | Shalon ................. A61B 5/0031 128/903 |
| 2006/0085047 A1 | 4/2006 | Unsworth et al. |
| 2006/0085049 A1 | 4/2006 | Cory et al. |
| 2006/0089683 A1 | 4/2006 | Hagglof et al. |
| 2006/0095088 A1 | 5/2006 | De Ridder |
| 2006/0173507 A1 | 8/2006 | Mrva et al. |
| 2006/0190057 A1 | 8/2006 | Reese |
| 2006/0251334 A1 | 11/2006 | Oba et al. |
| 2007/0021786 A1 | 1/2007 | Parnis et al. |
| 2007/0060922 A1 | 3/2007 | Dreyfuss |
| 2007/0203435 A1 | 8/2007 | Novak |
| 2007/0203547 A1 | 8/2007 | Costello et al. |
| 2007/0276449 A1 | 11/2007 | Gunter et al. |
| 2008/0009772 A1 | 1/2008 | Tyler et al. |
| 2008/0077192 A1 | 3/2008 | Harry et al. |
| 2008/0146980 A1 | 6/2008 | Rousso et al. |
| 2008/0147143 A1 | 6/2008 | Popovic et al. |
| 2008/0147146 A1 | 6/2008 | Wahlgren et al. |
| 2008/0172102 A1 | 7/2008 | Shalev |
| 2008/0312709 A1 | 12/2008 | Volpe et al. |
| 2009/0030476 A1 | 1/2009 | Hargrove |
| 2009/0076364 A1 | 3/2009 | Libbus et al. |
| 2009/0082829 A1 * | 3/2009 | Panken ................. A61N 1/36139 607/45 |
| 2009/0082831 A1 * | 3/2009 | Paul ................. A61N 1/36031 607/59 |
| 2009/0112214 A1 | 4/2009 | Philippon et al. |
| 2009/0131993 A1 | 5/2009 | Rousso et al. |
| 2009/0203972 A1 | 8/2009 | Heneghan et al. |
| 2009/0240303 A1 | 9/2009 | Wahlstrand et al. |
| 2009/0264789 A1 | 10/2009 | Molnar et al. |
| 2009/0270947 A1 | 10/2009 | Stone et al. |
| 2009/0326604 A1 | 12/2009 | Tyler et al. |
| 2010/0004715 A1 | 1/2010 | Fahey |
| 2010/0010585 A1 | 1/2010 | Davis et al. |
| 2010/0042180 A1 | 2/2010 | Mueller et al. |
| 2010/0057149 A1 | 3/2010 | Fahey |
| 2010/0087903 A1 | 4/2010 | Van Herk et al. |
| 2010/0094103 A1 | 4/2010 | Kaplan et al. |
| 2010/0114257 A1 | 5/2010 | Torgerson |
| 2010/0131028 A1 | 5/2010 | Hsu et al. |
| 2010/0198124 A1 | 8/2010 | Bhugra |
| 2010/0217349 A1 | 8/2010 | Fahey |
| 2010/0241464 A1 | 9/2010 | Amigo et al. |
| 2010/0274304 A1 | 10/2010 | Wang et al. |
| 2011/0066209 A1 | 3/2011 | Bodlaender et al. |
| 2011/0106213 A1 | 5/2011 | Davis et al. |
| 2011/0166622 A1 | 7/2011 | Crosson et al. |
| 2011/0190594 A1 | 8/2011 | Heit et al. |
| 2011/0224665 A1 | 9/2011 | Crosby et al. |
| 2011/0245711 A1 | 10/2011 | Katra et al. |
| 2011/0257468 A1 | 10/2011 | Oser et al. |
| 2011/0264171 A1 | 10/2011 | Torgerson |
| 2011/0276107 A1 | 11/2011 | Simon et al. |
| 2011/0282164 A1 | 11/2011 | Yang et al. |
| 2012/0010680 A1 | 1/2012 | Wei et al. |
| 2012/0108998 A1 | 5/2012 | Molnar et al. |
| 2012/0123227 A1 * | 5/2012 | Sun ................. A61B 5/14532 600/309 |
| 2012/0130449 A1 | 5/2012 | Carlyon et al. |
| 2012/0303077 A1 | 11/2012 | De Vincentiis |
| 2012/0319816 A1 | 12/2012 | Al-Ali |
| 2013/0079846 A1 * | 3/2013 | Single ................. H04R 25/505 607/57 |
| 2013/0096641 A1 | 4/2013 | Strother et al. |
| 2013/0116514 A1 | 5/2013 | Kroner et al. |
| 2013/0158627 A1 * | 6/2013 | Gozani ................. A61N 1/321 607/46 |
| 2013/0197341 A1 | 8/2013 | Grob et al. |
| 2013/0217998 A1 | 8/2013 | Mahfouz et al. |
| 2013/0317333 A1 | 11/2013 | Yang et al. |
| 2014/0005759 A1 | 1/2014 | Fahey et al. |
| 2014/0039450 A1 | 2/2014 | Green et al. |
| 2014/0057232 A1 | 2/2014 | Wetmore et al. |
| 2014/0081353 A1 | 3/2014 | Cook et al. |

(56) References Cited

U.S. PATENT DOCUMENTS

| | | |
|---|---|---|
| 2014/0088192 A1 | 3/2014 | Heller et al. |
| 2014/0107729 A1 | 4/2014 | Sumners et al. |
| 2014/0163444 A1 | 6/2014 | Ingvarsson et al. |
| 2014/0188194 A1* | 7/2014 | Schepis .............. A43B 7/1455 607/2 |
| 2014/0206976 A1* | 7/2014 | Thompson ............ G16Z 99/00 600/391 |
| 2014/0221797 A1* | 8/2014 | Bailey ................ A61B 5/0205 600/595 |
| 2014/0245784 A1 | 9/2014 | Proud et al. |
| 2014/0245791 A1 | 9/2014 | Proud et al. |
| 2014/0276236 A1* | 9/2014 | Swain ................ A61B 5/1038 600/592 |
| 2014/0276549 A1 | 9/2014 | Osorio |
| 2014/0296934 A1 | 10/2014 | Gozani et al. |
| 2014/0296935 A1 | 10/2014 | Ferree et al. |
| 2014/0309709 A1 | 10/2014 | Gozani et al. |
| 2014/0336725 A1 | 11/2014 | Nogueira |
| 2014/0336730 A1 | 11/2014 | Simon et al. |
| 2014/0343625 A1 | 11/2014 | O Laighin |
| 2014/0371547 A1 | 12/2014 | Gartenberg et al. |
| 2014/0371814 A1 | 12/2014 | Spizzirri et al. |
| 2014/0379045 A1 | 12/2014 | Rahimi et al. |
| 2015/0012068 A1* | 1/2015 | Bradley ............ A61N 1/36071 607/62 |
| 2015/0045853 A1* | 2/2015 | Alataris ............ A61N 1/36062 607/46 |
| 2015/0100107 A1 | 4/2015 | Kiani et al. |
| 2015/0157242 A1 | 6/2015 | Sabesan |
| 2015/0157868 A1 | 6/2015 | Franke et al. |
| 2015/0174402 A1* | 6/2015 | Thomas ............ A61N 1/36021 607/46 |
| 2015/0238094 A1 | 8/2015 | Lai et al. |
| 2015/0272511 A1 | 10/2015 | Najafi et al. |
| 2015/0306387 A1 | 10/2015 | Kong et al. |
| 2015/0321000 A1 | 11/2015 | Rosenbluth et al. |
| 2015/0328467 A1 | 11/2015 | Demers et al. |
| 2015/0335288 A1 | 11/2015 | Toth et al. |
| 2015/0335877 A1 | 11/2015 | Jeffery et al. |
| 2016/0007931 A1 | 1/2016 | Rubin et al. |
| 2016/0029891 A1* | 2/2016 | Lin .................... A61B 5/0532 340/10.5 |
| 2016/0113551 A1 | 4/2016 | Annegam et al. |
| 2016/0144174 A1 | 5/2016 | Ferree et al. |
| 2016/0151628 A1 | 6/2016 | Simon et al. |
| 2016/0166198 A1 | 6/2016 | Oddsson et al. |
| 2016/0189371 A1 | 6/2016 | Krishna Rao et al. |
| 2016/0213924 A1 | 7/2016 | Coleman et al. |
| 2016/0235981 A1* | 8/2016 | Southwell .......... A61N 1/36007 |
| 2016/0242646 A1 | 8/2016 | Obma |
| 2016/0243359 A1 | 8/2016 | Sharma |
| 2016/0250464 A1 | 9/2016 | Zschaeck et al. |
| 2016/0310730 A1* | 10/2016 | Martins .............. A61N 1/36031 |
| 2016/0367823 A1 | 12/2016 | Cowan et al. |
| 2017/0043160 A1 | 2/2017 | Goodall et al. |
| 2017/0056650 A1 | 3/2017 | Cohen et al. |
| 2017/0188864 A1* | 7/2017 | Drury ................ A61B 5/02427 |
| 2017/0188872 A1 | 7/2017 | Hughes et al. |
| 2017/0209693 A1* | 7/2017 | An ...................... A61N 1/0456 |
| 2017/0224990 A1 | 8/2017 | Goldwasser et al. |
| 2017/0238812 A1* | 8/2017 | Atlas ................ A61B 5/1117 |
| 2017/0368345 A1 | 12/2017 | Kong et al. |
| 2018/0000685 A1 | 1/2018 | Maloney et al. |
| 2018/0028808 A1 | 2/2018 | Ferree et al. |
| 2018/0132757 A1 | 5/2018 | Kong et al. |
| 2018/0177996 A1 | 6/2018 | Gozani et al. |
| 2018/0345014 A1 | 12/2018 | Gozani et al. |
| 2019/0001135 A1* | 1/2019 | Yoo ................... A61N 1/36132 |
| 2019/0022372 A1* | 1/2019 | Dar ....................... A61B 5/291 |
| 2019/0022386 A1* | 1/2019 | Gozani ................ A61N 1/0492 |
| 2019/0134393 A1 | 5/2019 | Wong et al. |
| 2020/0179694 A1 | 6/2020 | Kong et al. |
| 2020/0219615 A1 | 7/2020 | Rabin et al. |
| 2021/0128904 A1 | 5/2021 | Terekhov |
| 2021/0260374 A1* | 8/2021 | Gozani .............. A61N 1/36021 |

FOREIGN PATENT DOCUMENTS

| | | |
|---|---|---|
| CN | 1926496 | 3/2007 |
| CN | 101557788 | 10/2009 |
| CN | 101626804 | 1/2010 |
| CN | 102202131 | 9/2011 |
| CN | 102355847 | 2/2012 |
| CN | 102740919 | 10/2012 |
| DE | 102010052710 | 5/2012 |
| EP | 0 971 653 | 1/2000 |
| EP | 1 985 277 | 2/2015 |
| JP | 61-171943 | 10/1986 |
| JP | 4-347140 | 12/1992 |
| JP | 9-117453 | 5/1997 |
| JP | 2000-167067 | 6/2000 |
| JP | 2005-34402 | 2/2005 |
| JP | 2005-81068 | 3/2005 |
| JP | 2006-68300 | 3/2006 |
| JP | 4185846 | 9/2008 |
| WO | WO 97/42999 | 11/1997 |
| WO | WO 99/64105 | 12/1999 |
| WO | WO 03/051453 | 6/2003 |
| WO | WO 2004/078132 | 9/2004 |
| WO | WO 2007/061746 | 5/2007 |
| WO | WO 2008/079757 | 7/2008 |
| WO | WO 2008/088985 | 7/2008 |
| WO | WO 2009/036313 | 3/2009 |
| WO | WO 2011/075179 | 6/2011 |
| WO | WO 2011/137193 | 11/2011 |
| WO | WO 2012/116407 | 9/2012 |
| WO | WO 2013/028960 | 2/2013 |
| WO | WO 2014/172381 | 10/2014 |
| WO | WO 2015/123373 | 8/2015 |
| WO | WO 2016/201366 | 12/2016 |
| WO | WO 2018/089655 | 5/2018 |
| WO | WO 2020/033883 | 2/2020 |

OTHER PUBLICATIONS

Amazon, "Quell Wearable Pain Relief Technology Starter Kit", Oct. 18, 2017. http://www.amazon.com/Quell-Wearable-ReliefTechnology-Starter/dp/B075YVCLZT/ref=cm_cr_arp_d_product_top?ie=UTF8. Shown on p. 1. (Year: 2017).

Amft, O. et al., Sensing Muscle Activities with Body-Worn Sensors, Conference Paper, May 2006.

Ancoli-Israel, S. et al., The Role of Actigraphy in the Study of Sleep and Circadian Rhythms, Sleep, 2003, 26(3), p. 342-392.

Aurora, R. et al., The Treatment of Restless Legs Syndrome and Periodic Limb Movement Disorder in Adults—An Update for 2012: Practice Parameters with an Evidence-Based Systematic Review and Meta-Analyses, Sleep, 2012, vol. 35, No. 8, p. 1039-1062.

Barbarisi, Manlio et al., Pregabalin and Transcutaneous Electrical Nerve Stimulation for Postherpetic Neuralgia Treatment, The Clinical Journal of Pain, Sep. 2010;26(7):567-572.

Bifulco, P. et al., A Stretchable, Conductive Rubber Sensor to Detect Muscle Contraction for Prosthetic Hand Control, The 6th IEEE International Conference on E-Health and Bioengineering—EHB 2017, Jun. 22-24, 2017, pp. 173-176.

Bjordal JM et al., Transcutaneous electrical nerve stimulation (TENS) can reduce postoperative analgesic consumption. A meta-analysis with assessment of optimal treatment parameters for post-operative pain, Europe Journal of Pain, 2003, vol. 7(2): 181-188.

Bloodworth DM et al., Comparison of stochastic vs. conventional transcutaneous electrical stimulation for pain modulation in patients with electromyographically documented radiculopathy, American Journal of Physical Medicine & Rehabilitation, 2004, vol. 83(8): 584-591.

Bonnet, M. et al., Recording and Scoring Leg Movements, Sleep, 1993, vol. 16, No. 8, p. 748-759.

Boyle, J. et al., Randomized, Placebo-Controlled Comparison of Amitriptyline, Duloxetine, and Pregabalin in Patients With Chronic Diabetic Peripheral Neuropathic Pain, Diabetes Care, 2012, vol. 35, p. 2451-2458.

(56) References Cited

OTHER PUBLICATIONS

Chandran P et al., Development of opioid tolerance with repeated transcutaneous electrical nerve stimulation administration, Pain, 2003, vol. 102: 195-201.
Chen CC et al., A comparison of transcutaneous electrical nerve stimulation (TENS) at 3 and 80 pulses per second on cold-pressor pain in healthy human participants, Clinical Physiology and Functioning Imaging, 2010, vol. 30(4): 260-268.
Chen CC et al., An investigation into the effects of frequency-modulated transcutaneous electrical nerve stimulation (TENS) on experimentally-induced pressure pain in healthy human participants, The Journal of Pain, 2009, vol. 10(10): 1029-1037.
Chen CC et al., Differential frequency effects of strong nonpainful transcutaneous electrical nerve stimulation on experimentally induced ischemic pain in healthy human participants, The Clinical Journal of Pain, 2011, vol. 27(5): 434-441.
Chen CC et al., Does the pulse frequency of transcutaneous electrical nerve stimulation (TENS) influence hypoalgesia? A systematic review of studies using experimantal pain and healthy human participants, Physiotherapy, 2008, vol. 94: 11-20.
Claydon LS et al., Dose-specific effects of transcutaneous electrical nerve stimulation on experimental pain, Clinical Journal of Pain, 2011, vol. 27(7): 635-647.
Cole, R.J. et al., Automatic Sleep/Wake Identification From Wrist Activity, Sleep, 1992, 15(5), p. 461-469.
Cruccu G. et al., EFNS guidelines on neurostimulation therapy for neuropathic pain, European Journal of Neurology, 2007, vol. 14: 952-970.
Dailey DL et al., Transcutaneous Electrical Nerve Stimulation (TENS) Reduces Pain, Fatigue, and Hyperalgesia while Restoring Central Inhibition in Primary Fibromyalgia, Pain, Nov. 2013, vol. 154, No. 11, pp. 2554-2562.
Dailey, D. et al., Transcutaneous Electrical Nerve Stimulation Reduces Movement-Evoked Pain and Fatigue: A Randomized, Controlled Trial, Arthritis & Rheumatology, May 2020, vol. 72, No. 5, pp. 824-836.
Davies HTO et al., Diminishing returns or appropriate treatment strategy?—an analysis of short-term outcomes after pain clinic treatment, Pain, 1997, vol. 70: 203-208.
Desantana JM et al., Effectiveness of transcutaneous electrical nerve stimulation for treatment of hyperalgesia and pain, Curr Rheumatol Rep. 2008, vol. 10(6): 492-499.
Dubinsky RM et al., Assessment Efficacy of transcutaneous electric nerve stimulation in the treatment of pain in neurologic disorders (an evidence-based review): Report of the therapeutics and technology assessment subcommittee of the american academy of neurology, Neurology, 2010, vol. 74: 173-176.
Fary RE et al., Monophasic electrical stimulation produces high rates of adverse skin reactions in healthy subjects, Physiotherapy Theory and Practice, 2011, vol. 27(3): 246-251.
Fishbain, David A. et al. Does Pain Mediate the Pain Interference with Sleep Problem in Chronic Pain? Findings from Studies for Management of Diabetic Peripheral Neuropathic Pain with Duloxetine, Journal of Pain Symptom Management, Dec. 2008; 36(6):639-647.
Fishbain, David A. et al., Transcutaneous Electrical Nerve Stimulation (TENS) Treatment Outcome in Long-Term Users, The Clinical Journal of Pain, Sep. 1996; 12(3):201-214.
Food and Drug Administration, Draft Guidance for Industry and Staff: Class II Special Controls Guidance Document: Transcutaneous Electrical Nerve Stimulator for Pain Relief, Apr. 5, 2010.
Garrison DW et al., Decreased activity of spontaneous and noxiously evoked dorsal horn cells during transcutaneous electrical nerve stimulation (TENS), Pain, 1994, vol. 58: 309-315.
Gilron, I. et al., Chronobiological Characteristics of Neuropathic Pain: Clinical Predictors of Diurnal Pain Rhythmicity, The Clinical Journal of Pain, 2013.
Gozani SN et al., Fixed-Site High-Frequency Transcutaneous Electrical Nerve Stimulation for Treatment of Chronic Low Back and Lower Extremity Pain, Journal of Pain Research, 2016, vol. 9, pp. 469-479.

Hausdorff, J.M. et al., Gait Variability and Fall Risk in Community-Living Older Adults: A 1-Year Prospective Study, Arch Phys Med Rehabil, Aug. 2001, vol. 82, pp. 1050-1056.
Hori, T. et al., Skin Potential Activities and Their Regional Differences During Normal Sleep in Humans, The Japanese Journal of Physiology, 1970, vol. 20, p. 657-671.
Jelinek HF et al., Electric pulse frequency and magnitude of perceived sensation during electrocutaneous forearm stimulation, Arch Phys Med Rehabil, 2010, vol. 91: 1372-1382.
Jin DM et al., Effect of transcutaneous electrical nerve stimulation on symptomatic diabetic peripheral neuropathy: a meta-analysis of randomized controlled trials, Diabetes Research and Clinical Practice, 2010, vol. 89: 10-15.
Johnson MI et al., Analgesic effects of different frequencies of transcutaneous electrical nerve stimulation on cold-induced pain in normal subjects, Pain, 1989, vol. 39: 231-236.
Johnson MI et al., Transcutaneous Electrical Nerve Stimulation (TENS) and TENS-like devices: do they provide pain relief?, Pain Reviews, 2001, vol. 8: 7-44.
Johnson MI et al., Transcutaneous electrical nerve stimulation for the management of painful conditions: focus on neuropathic pain, Expert Review of Neurotherapeutics, 2011, vol. 11(5): 735-753.
Johnson, M.I. et al., An in-depth study of long-term users of transcutaneous electrical nerve stimulation (TENS). Implications for clinical use of TENS. Pain. Mar. 1991;44(3):221-229.
Kaczmarek, Kurt A. et al.. Electrotactile and Vibrotactile Displays for Sensory Substitution Systems. IEEE Trans. Biomed. Eng. Jan. 1991;38 (1):1-16.
Kantor G et al., The effects of selected stimulus waveforms on pulse and phase characteristics at sensory and motor thresholds, Physical Therapy, 1994, vol. 74(10): 951-962.
Keller, Thierry et al., Electrodes for transcutaneous (surface) electrical stimulation. J. Automatic Control, University of Belgrade. 2008; 18(2):35-45.
Koumans, A. J. R. et al., Electrodermal Levels and Fluctuations During Normal Sleep, Psychophysiology, 1968, 5(3), p. 300-306.
Kovacevic-Ristanovic, R. et al., Nonpharmacologic Treatment of Periodic Leg Movements in Sleep, Arch. Phys. Med. Rehabil., 1991, vol. 72, p. 385-389.
Kripke, D.F. et al., Wrist Actigraphic Scoring for Sleep Laboratory Patients: Algorithm Development, Journal of Sleep Research, 2010, 19(4), p. 612-619.
Law PPW et al., Optimal stimulation frequency of transcutaneous electrical nerve stimulation on people with knee osteoarthritis, J Rehabil Med, 2004, vol. 36: 220-225.
Leonard G et al., Deciphering the role of endogenous opioids in high-frequency TENS using low and high doses of naloxone, Pain, 2010, vol. 151: 215-219.
Levy et al., A comparison of two methods for measuring thermal thresholds in diabetic neuropathy, Journal of Neurology, Neurosurgery, and Psychiatry, 1989, vol. 52: 1072-1077.
Lopes, L. et al., Restless Legs Syndrome and Quality of Sleep in Type 2 Diabetes, Diabetes Care, 2005, vol. 28, No. 11, p. 2633-2636.
Lykken, D.T., Properties of Electrodes Used in Electrodermal Measurement J. Comp. Physiol. Psychol. Oct. 1959; 52:629-634.
Lykken, D.T., Square-Wave Analysis of Skin Impedance. Psychophysiology. Sep. 1970; 7(2):262-275.
Macfarlane, T. et al., Whether the weather influences pain? Results from EpiFunD study in North West England, Rheumatology, 2010, vol. 49, pp. 1513-1520.
Melzack R et al., Pain mechanisms: A New Theory, Science, 1965, vol. 150(3699): 971-979.
Moran F et al., Hypoalgesia in response to transcutaneous electrical nerve stimulation (TENS) depends on stimulation intensity, The Journal of Pain, 2011, vol. 12(8): 929-935.
Nightingale, S., The neuropathic pain market, Nature Reviews, 2012, vol. 11, p. 101-102.
Okamoto-Mizuno. K. et al., Effects of thermal environment on sleep and circadian rhythm, Journal of Physiological Anthropology, 2012, vol. 31, No. 14, pp. 1-9.

(56) References Cited

OTHER PUBLICATIONS

Oosterhof, Jan et al., Outcome of transcutaneous electrical nerve stimulation in chronic pain: short-term results of a double-blind, randomised, placebo-controlled trial. J. Headache Pain. Sep. 2006; 7 (4):196-205.

Oosterhof, Jan et al., The long-term outcome of transcutaneous electrical nerve stimulation in the treatment for patients with chronic pain: a randomized, placebo-controlled trial. Pain Pract. Sep. 2012; 12(7):513-522.

Ossipov MH et al., Central Modulation of Pain, The Journal of Clinical Investigation, Nov. 2010, vol. 120, No. 11, pp. 3779-3787.

Pantaleao MA et al., Adjusting pulse amplitude during transcutaneous electrical nerve stimulation (TENS) application produces greater hypoalgesia, The Journal of Pain, 2011, vol. 12(5):581-590.

Paquet, J. et al., Wake Detection Capacity of Actigraphy During Sleep, Sleep, 2007, 30(10), p. 1362-1369.

Pieber K et al., Electrotherapy for the treatment of painful diabetic peripheral neuropathy: a review, Journal of Rehabilitation Medicine, 2010, vol. 42: 289-295.

Raskin, J. et al., A Double-Blind, Randomized Multicenter Trial Comparing Duloxetine with Placebo in the Management of Diabetic Peripheral Neuropathic Pain, Pain Medicine, 2005, 6(5), p. 346-356.

Sadeh, A., The Role and Validity of Actigraphy in Sleep Medicine: An Update, Sleep Medicine Reviews, 2011, vol. 15, p. 259-267.

Sadosky, A. et al., Burden of Illness Associated with Painful Diabetic Peripheral Neuropathy Among Adults Seeking Treatment in the US: Results from a Retrospective Chart Review and Cross-Sectional Survey, Diabetes, Metabolic Syndrome and Obesity: Targets and Therapy, 2013, vol. 6, p. 79-92.

Sano, A et al, Quantitative analysis of wrist electrodermal activity during sleep, International Journal of Psychophysiology, 2014, vol. 94, pp. 382-389.

Scherder, E. J. A. et al., Transcutaneous Electrical Nerve Stimulation (TENS) Improves the Rest-Activity Rhythm in Midstage Alzheimer's Disease, Behavioral Brain Research, 1999, vol. 101, p. 105-107.

Sheridan et al., Some Factors Influencing the Threshold of the Electrocutaneous Stimulus, Perceptual and Motor Skills, 1966, vol. 22, pp. 647-654.

Susi et al., Motion Mode Recognition and Step Detection Algorithms for Mobile Phone Users, Sensors, Jan. 24, 2013, vol. 13, pp. 1539-1562.

Taborri et al., A Novel HMM Distributed Classifier for the Detection of Gait Phases by Means of a Wearable Inertial Sensor Network, Sensors, Sep. 2014, vol. 14, pp. 16212-16234.

Timmermans, E. et al., Self-perceived weather sensitivity and joint pain in older people with osteoarthritis in six European countries: results from the European Project on OSteoArthritis (EPOSA), BMC Musculoskeletal Disorders, 2014,, vol. 15, No. 66, pp. 1-11.

Tryon, W. W., Issues of Validity in Actigraphic Sleep Assessment, Sleep, 2004, 27(1), p. 158-165.

Tsai, Y. et al., Impact of Subjective Sleep Quality on Glycemic Control in Type 2 Diabetes Mellitus, Family Practice, 2012, vol. 29, p. 30-35.

Van Boxtel, A., Skin resistance during square-wave electrical pulses of 1 to 10 mA. Med. Biol. Eng. Comput. Nov. 1977; 15(6):679-687.

Van Someren, E. J. W. et al., Gravitational Artefact in Frequency Spectra of Movement Acceleration: Implications for Actigraphy in Young and Elderly Subjects, Journal of Neuroscience Methods, 1996, vol. 65, p. 55-62.

Waeber, R. et al., Bisection Search with Noisy Responses, Siam J. Control Optim., 2013, vol. 51, No. 3, pp. 2261-2279.

Webster, J. B. et al., An Activity-Based Sleep Monitor System for Ambulatory Use, Sleep, 1982, 5(4), p. 389-399.

Zelman, D. C. et al., Sleep Impairment in Patients With Painful Diabetic Peripheral Neuropathy, The Clinical Journal of Pain, 2006, 22(8), p. 681-685.

Zucconi, M. et al., The official World Association of Sleep Medicine (WASM) standards for recording and scoring periodic leg movements in sleep (PLMS) and wakefulness (PLMW) developed in collaboration with a task force from the International Restless Legs Syndrome Study Group (IRLSSG), Sleep Medicine, 2006, vol. 7, p. 175-183.

\* cited by examiner

APPARATUS AND METHOD FOR BUTTON-FREE CONTROL OF A WEARABLE TRANSCUTANEOUS ELECTRICAL NERVE STIMULATOR USING INTERACTIVE GESTURES AND OTHER MEANS

REFERENCE TO PENDING PRIOR PATENT APPLICATIONS

This patent application is a continuation of pending prior U.S. patent application Ser. No. 16/010,974, filed Jun. 18, 2018 by Neurometrix, Inc. for APPARATUS AND METHOD FOR BUTTON-FREE CONTROL OF A WEARABLE TRANSCUTANEOUS ELECTRICAL NERVE STIMULATOR USING INTERACTIVE GESTURES AND OTHER MEANS, issued as U.S. Pat. No. 10,940,311, which patent application:

(1) is a continuation-in-part of prior U.S. patent application Ser. No. 15/824,351, filed Nov. 28, 2017 by Neurometrix, Inc. and Thomas Ferree et al. for TRANSCUTANEOUS ELECTRICAL NERVE STIMULATOR WITH USER GESTURE DETECTOR AND ELECTRODE-SKIN CONTACT DETECTOR, WITH TRANSIENT MOTION DETECTOR FOR INCREASING THE ACCURACY OF THE SAME, issued as U.S. Pat. No. 10,130,810, which patent application is a continuation of prior U.S. patent application Ser. No. 14/269,887, filed May 5, 2014 by Neurometrix, Inc. and Thomas Ferree et al. for TRANSCUTANEOUS ELECTRICAL NERVE STIMULATOR WITH USER GESTURE DETECTOR AND ELECTRODE-SKIN CONTACT DETECTOR, WITH TRANSIENT MOTION DETECTOR FOR INCREASING THE ACCURACY OF THE SAME, issued as U.S. Pat. No. 9,827,420, which in turn:

(i) is a continuation-in-part of prior U.S. patent application Ser. No. 14/230,648, filed Mar. 31, 2014 by NeuroMetrix, Inc. and Shai Gozani et al. for DETECTING CUTANEOUS ELECTRODE PEELING USING ELECTRODE-SKIN IMPEDANCE, issued as U.S. Pat. No. 9,474,898, which claims benefit of prior U.S. Provisional Patent Application Ser. No. 61/806,481, filed Mar. 29, 2013 by NeuroMetrix, Inc. and Shai Gozani for DETECTING ELECTRODE PEELING BY RELATIVE CHANGES IN SKIN-ELECTRODE IMPEDANCE;

(ii) is a continuation-in-part of prior U.S. patent application Ser. No. 14/253,628, filed Apr. 15, 2014 by Neurometrix, Inc. and Shai Gozani et al. for TRANSCUTANEOUS ELECTRICAL NERVE STIMULATOR WITH AUTOMATIC DETECTION OF USER SLEEP-WAKE STATE, issued as U.S. Pat. No. 10,279,179, which claims benefit of prior U.S. Provisional Patent Application Ser. No. 61/811,864, filed Apr. 15, 2013 by NeuroMetrix, Inc. and Shai Gozani for TRANSCUTANEOUS ELECTRICAL NERVE STIMULATOR WITH AUTOMATIC DETECTION OF PATIENT SLEEP-WAKE STATE;

(iii) claims benefit of prior U.S. Provisional Patent Application Ser. No. 61/819,159, filed May 3, 2013 by NeuroMetrix, Inc. and Thomas Ferree et al. for TAP DETECTOR WITH HIGH SENSITIVITY AND SPECIFICITY FOR A WEARABLE TRANSCUTANEOUS ELECTRICAL NERVE STIMULATOR; and (iv) claims benefit of prior U.S. Provisional Patent Application Ser. No. 61/858,150, filed Jul. 25, 2013 by NeuroMetrix, Inc. and Andres Aguirre et al. for MOVEMENT REGULATED TRIP CONDITIONS IN A WEARABLE TRANSCUTANEOUS ELECTRICAL NERVE STIMULATOR; and (2) claims benefit of prior U.S. Provisional Patent Application Ser. No. 62/524,195, filed Jun. 23, 2017 by Neurometrix, Inc. and Shai N. Gozani et al. for BUTTON-FREE CONTROL OF A WEARABLE TRANSCUTANEOUS ELECTRICAL NERVE STIMULATOR USING INTERACTIVE GESTURES AND OTHER MEANS.

The ten (10) above-identified patent applications are hereby incorporated herein by reference.

FIELD OF THE INVENTION

This invention relates generally to Transcutaneous Electrical Nerve Stimulation (TENS) devices that deliver electrical currents across the intact skin of a user via electrodes to provide symptomatic relief of pain. More specifically, this invention discloses apparatus and methods for controlling the operation of a TENS device without requiring mechanical actuators (e.g., physical push-buttons).

BACKGROUND OF THE INVENTION

Transcutaneous electrical nerve stimulation (TENS) is the delivery of electricity (i.e., electrical stimulation) across the intact surface of a user's skin in order to activate sensory nerve fibers. The most common application of TENS therapy is to provide analgesia, such as for alleviation of chronic pain. Other applications of TENS therapy include, but are not limited to, reducing the symptoms of restless leg syndrome, decreasing nocturnal muscle cramps, and providing relief from generalized pruritus.

In conventional TENS, electrodes are placed on the skin within, adjacent to, or proximal to, the area of pain. In fixed-site high-frequency TENS, the electrodes are placed in an anatomically and physiologically optimal area (e.g., the upper calf of the user) that results in widespread analgesia. An electrical circuit generates stimulation pulses with specified characteristics. One or more pairs of electrodes, placed on the patient's skin, transduce the electrical pulses and thereby stimulate underlying nerves to relieve pain.

A conceptual model for how sensory nerve stimulation leads to pain relief was proposed by Melzack and Wall in 1965. Their theory proposes that the activation of sensory nerves ($A\beta$ fibers) closes a "pain gate" in the spinal cord that inhibits the transmission of pain signals carried by nociceptive afferents (C and $A\delta$ fibers) to the brain. In the past 20 years, anatomic pathways and molecular mechanisms that may underlie the pain gate have been identified. Sensory nerve stimulation (e.g., via TENS) activates the descending pain inhibition system, primarily the periaqueductal gray (PAG) and rostroventral medial medulla (RVM) located in the midbrain and medulla sections of the brainstem, respectively. The PAG has neural projections to the RVM, which in turn has diffuse bilateral projections into the spinal cord dorsal horn that inhibit ascending pain signal transmission.

TENS is typically delivered in short discrete pulses, with each pulse typically being several hundred microseconds in duration, at frequencies of between about 10 Hz and about 150 Hz, through hydrogel electrodes placed on the user's body. TENS is characterized by a number of electrical parameters including the amplitude and shape of the stimulation pulse (which combine to establish the pulse charge), the frequency and pattern of the pulses, the duration of a therapy session, and the interval between therapy sessions. All of these parameters are correlated to the therapeutic dose. For example, higher amplitude and longer pulses (i.e., larger pulse charges) increase the dose, whereas shorter therapy sessions decrease the dose. Clinical studies suggest that pulse charge and therapy session duration have the greatest impact on therapeutic dose.

User control over a TENS device is typically provided with mechanical actuators directly wired to the electronic circuits regulating electrical stimulation. These actuators are usually push-buttons and/or dials. To achieve maximum pain relief (i.e., hypoalgesia), TENS needs to be delivered at an adequate stimulation intensity. Intensities below the threshold of sensation are not clinically effective. The optimal therapeutic intensity is often described as one that is "strong yet comfortable". Most TENS devices rely on the user to set the stimulation intensity, usually through a manual intensity control comprising an analog intensity knob or digital intensity control push-buttons.

Pain relief from TENS stimulation usually begins within 15 minutes of the stimulation onset and may last up to an hour following the completion of the stimulation period (which is also known as a "therapy session"). Each therapy session typically runs for 30-60 minutes. To maintain maximum pain relief (i.e., hypoalgesia), TENS therapy sessions typically need to be initiated at regular intervals.

Recently, wearable TENS devices have been introduced (e.g., the SENSUS® and Quell® TENS devices from NeuroMetrix, Inc. of Waltham, Mass.) where the device is intended to be worn on the body of a user for prolonged periods of time, including while sleeping. In order to be comfortable and wearable under clothing, such devices must have a low profile. It is therefore advantageous that these devices have no mechanical actuators (e.g., push-buttons). Furthermore, it is difficult to locate and actuate a push-button under clothing unless the push-button is large. However, a large push-button increases the size, thickness, and manufacturing complexity of the device, thereby decreasing the wearability of the device. Moreover, push-buttons and other mechanical actuators are prone to accidental activation such as when the user is sleeping.

A smartphone "App" can be used to control operation of a TENS device wirelessly through a Bluetooth or similar wireless communication protocol. This requires the TENS device to maintain an active communication link with the smartphone App in order to respond to control commands from the smartphone App and to exchange information between the TENS device and the App. Maintaining a continuous active communication link between the TENS device and the smartphone App can be expensive in terms of battery power consumption, leading to the need for frequent recharges and user inconvenience.

To improve wearability and comfort, portable TENS devices must have a small total volume and low profile. Volume requirements put an upper limit on the physical size of a rechargeable battery contained within the TENS device. The capacity of the battery powering the TENS device, which is typically somewhat proportional to the size of the battery, is thus limited in such wearable TENS devices. To extend battery life, it is necessary to transition the TENS device from an active to a power-saving state when the TENS device is not in use, and to transition the TENS device back to an active state when the TENS device is to be used, all in an intuitive and reliable manner.

SUMMARY OF THE INVENTION

The present invention comprises the provision and use of a novel TENS device without requiring the use of mechanical actuators (e.g., push-buttons, switches, dials, etc.). The states (active and power-saving) and the operation of the TENS device are controlled through intentional gestures and other means. In one preferred form of the invention, a three-axis accelerometer is incorporated into the TENS device and measures the motion and orientation of the TENS device caused by user hand gestures such as taps, flicks, and shakes, and alters the device states (active and power-saving) and operations accordingly.

Other control means may be provided for controlling the state and operation of the TENS device via wireless connections, including RFID (radio-frequency identification tag) and other similar near-field communication devices (including an App running on a Bluetooth-enabled smartphone).

Additional device control schemes include the automatic initiation of therapy upon device placement on the skin of the user, and transitions into and out of a power-saving mode based on general movements sensed by the TENS device.

In one preferred form of the invention, there is provided apparatus for transcutaneous electrical nerve stimulation in a user, said apparatus comprising:

a stimulator for electrically stimulating at least one nerve;

a stimulator housing;

a monitor for monitoring transient motion of said stimulator housing;

an analyzer for analyzing transient motion monitored by said monitor for determining whether transient motion of said stimulator housing has occurred; and a controller for automatically transitioning at least one of said stimulator, said monitor, and said analyzer between a standby mode and a power save mode;

wherein said power save mode supports a subset of the functionality of said stimulator and said monitor which is available in said standby mode so as to conserve battery power in said power save mode.

In another preferred form of the invention, there is provided apparatus for transcutaneous electrical nerve stimulation in a user, said apparatus comprising:

a stimulator for electrically stimulating at least one nerve;

a pair of electrodes connectable to said stimulator for electrical stimulation of said at least one nerve;

an on-skin detector electrically connected to said stimulator for monitoring impedance between said pair of electrodes and the body of a user in order to determine the on-skin status of said pair of electrodes; and a controller for automatically transitioning said stimulator between a standby mode and an active mode;

wherein said stimulator delivers electrical stimulation to the user in said active mode.

In another preferred form of the invention, there is provided apparatus for transcutaneous electrical nerve stimulation in a user, said apparatus comprising:

a stimulator for electrically stimulating at least one nerve;

a stimulator housing;

a monitor for monitoring the transient motion of said stimulator housing;

a remote controller for indicating the proximity of a hand of a user to said monitor;

an analyzer for analyzing transient motion monitored by said monitor for determining whether transient motion of said stimulator housing is caused by an intentional hand gesture by a user; and a controller for automatically modifying operation of said stimulator in response to said intentional hand gesture;

wherein said proximity indicated by said remote controller modifies operation of said analyzer.

In another preferred form of the invention, there is provided a method for controlling transcutaneous electrical nerve stimulation without mechanical actuators or buttons, said method comprising the steps of:

providing apparatus for transcutaneous electrical nerve stimulation in a user, said apparatus comprising:
a stimulator for electrically stimulating at least one nerve;
a stimulator housing;
a monitor for monitoring transient motion of said stimulator housing;
an analyzer for analyzing transient motion monitored by said monitor; and
a controller for automatically transitioning at least one of said stimulator, said monitor, and said analyzer between a standby mode and a power save mode;
wherein said power save mode supports a subset of the functionality of said stimulator and said monitor which is available in said standby mode so as to conserve battery power in said power save mode;
determining presence of transient motion based on measurements from said monitor; and
transitioning at least one of said stimulator, said monitor, and said analyzer between said standby mode and said power save mode.

In another preferred form of the invention, there is provided a method for controlling transcutaneous electrical nerve stimulation without mechanical actuators or buttons, said method comprising the steps of:

providing apparatus for transcutaneous electrical nerve stimulation in a user, said apparatus comprising:
a stimulator for electrically stimulating at least one nerve;
a pair of electrodes connectable to said stimulator for electrical stimulation of the at least one nerve;
an on-skin detector electrically connected to said stimulator for monitoring the on-skin status of said pair of electrodes; and
a controller for automatically transitioning the stimulator between a standby mode and an active mode;
determining on-skin status of said pair of electrodes; and
transitioning said stimulator between said standby mode and said active mode.

In another preferred form of the invention, there is provided a method for controlling transcutaneous electrical nerve stimulation without mechanical actuators or buttons, said method comprising the steps of:

providing apparatus for transcutaneous electrical nerve stimulation in a user, said apparatus comprising:
a stimulator for electrically stimulating at least one nerve;
a stimulator housing;
a monitor for monitoring transient motion of said stimulator housing;
a remote controller for indicating the proximity of a hand of the user to said monitor;
an analyzer for analyzing transient motion monitored by said monitor for determining whether the transient motion of said stimulator is caused by an intentional hand gesture by the user; and
a controller for automatically modifying operation of said stimulator in response to said intentional hand gesture;
modifying operation of said analyzer based on proximity information from said remote controller;
determining the presence of an intentional hand gesture by the user based on measurements from said monitor; and
controlling operation of said stimulator based on said intentional hand gesture.

In another preferred form of the invention, there is provided apparatus for transcutaneous electrical nerve stimulation in a user, said apparatus comprising:
a stimulator for electrically stimulating at least one nerve;
a stimulator housing;
a monitor for monitoring the transient motion of said stimulator housing;
an analyzer for analyzing transient motion monitored by said monitor for determining whether transient motion of said stimulator housing is caused by an intentional gesture by a user; and
a controller for automatically modifying operation of said stimulator in response to said intentional gesture.

In another preferred form of the invention, there is provided a method for controlling transcutaneous electrical nerve stimulation without mechanical actuators or buttons, said method comprising the steps of:

providing apparatus for transcutaneous electrical nerve stimulation in a user, said apparatus comprising:
a stimulator for electrically stimulating at least one nerve;
a stimulator housing;
a monitor for monitoring transient motion of said stimulator housing;
an analyzer for analyzing transient motion monitored by said monitor for determining whether the transient motion of said stimulator is caused by an intentional gesture by the user; and
a controller for automatically modifying operation of said stimulator in response to said intentional gesture;
determining the presence of an intentional hand gesture by the user based on measurements from said monitor; and
controlling operation of said stimulator based on said intentional gesture.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

The TENS Device in General

The present invention comprises the provision and use of a novel TENS device with a stimulator designed to be placed on a user's upper calf (or other anatomical location) and a pre-configured electrode array designed to provide electrical stimulation to at least one nerve disposed in the user's upper calf (or other anatomical location). A key feature of the present invention is that the novel TENS device contains no mechanical actuators (e.g., push-buttons, switches, dials, etc.) for controlling operation of the TENS device.

Figure 1:
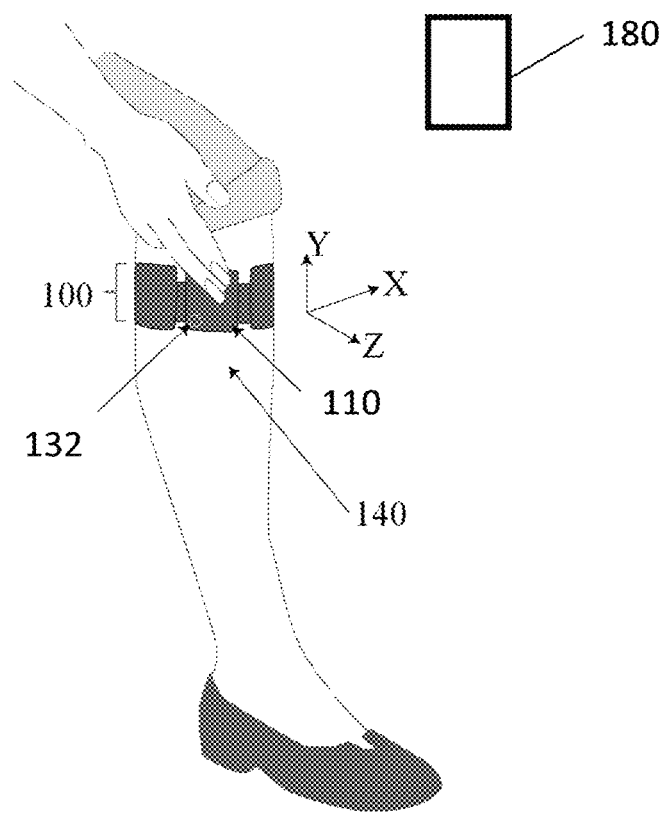
FIG. 1 is a schematic view showing a novel TENS device formed in accordance with the present invention, wherein the novel TENS device is mounted to the upper calf of a user, and also showing the coordinate system of an accelerometer incorporated in the novel TENS device.

More particularly, and looking now at FIG. 1, there is shown a novel TENS device 100 formed in accordance with the present invention, with novel TENS device 100 being shown worn on a user's upper calf 140. A user may wear TENS device 100 on one leg or on both legs (either one at a time or simultaneously), or a user may wear a TENS device 100 on another area of the body separate from, or in addition to, a TENS device 100 worn on one leg (or both legs) of the user.

Figure 2:
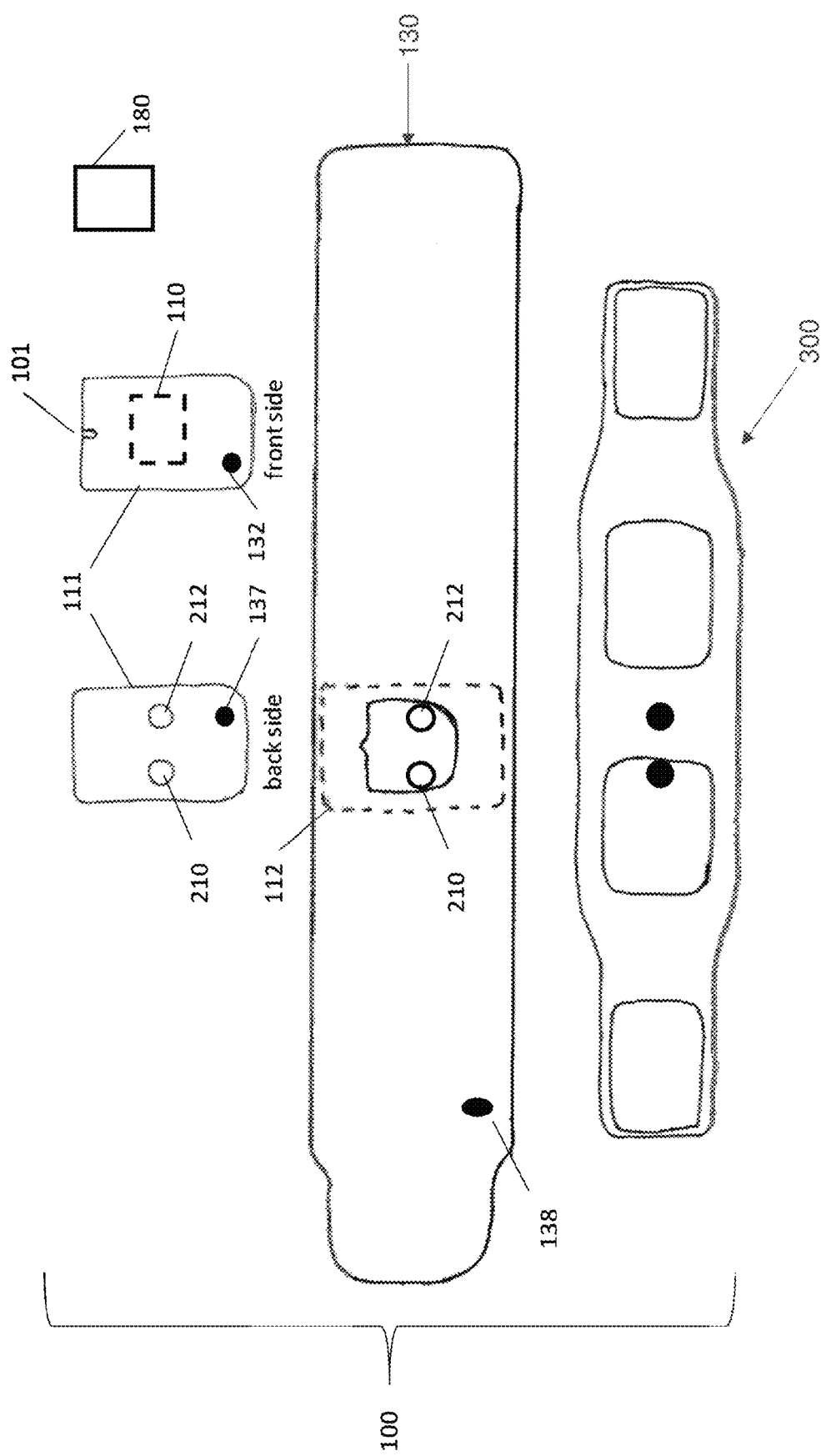
FIG. 2 is a schematic view showing the novel TENS device of FIG. 1 in greater detail.

Looking next at FIG. 2, TENS device 100 is shown in greater detail. TENS device 100 preferably comprises three primary components: a stimulator 110, a strap 130, and an electrode array 300 (comprising a cathode electrode and an anode electrode appropriately connected to stimulator 110). In a preferred form of the present invention, a stimulator housing 111 houses the TENS stimulation circuitry and one or more user interface elements 101 (e.g., an LED). Both the front side and the back side of stimulator housing 111 are shown in FIG. 2. Strap 130 comprises a pocket 112 for receiving stimulator housing 111 of stimulator 110. TENS device 100 also comprises an accelerometer 132 (see FIGS. 2 and 4), preferably in the form of a MEMS digital accelerometer microchip (e.g., Freescale MMA8451Q), for detecting (i) user gestures such as taps to stimulator housing 111, (ii) user leg and body orientation, and (iii) user leg and body motion when the device is disposed on the user's skin.

Figure 4:
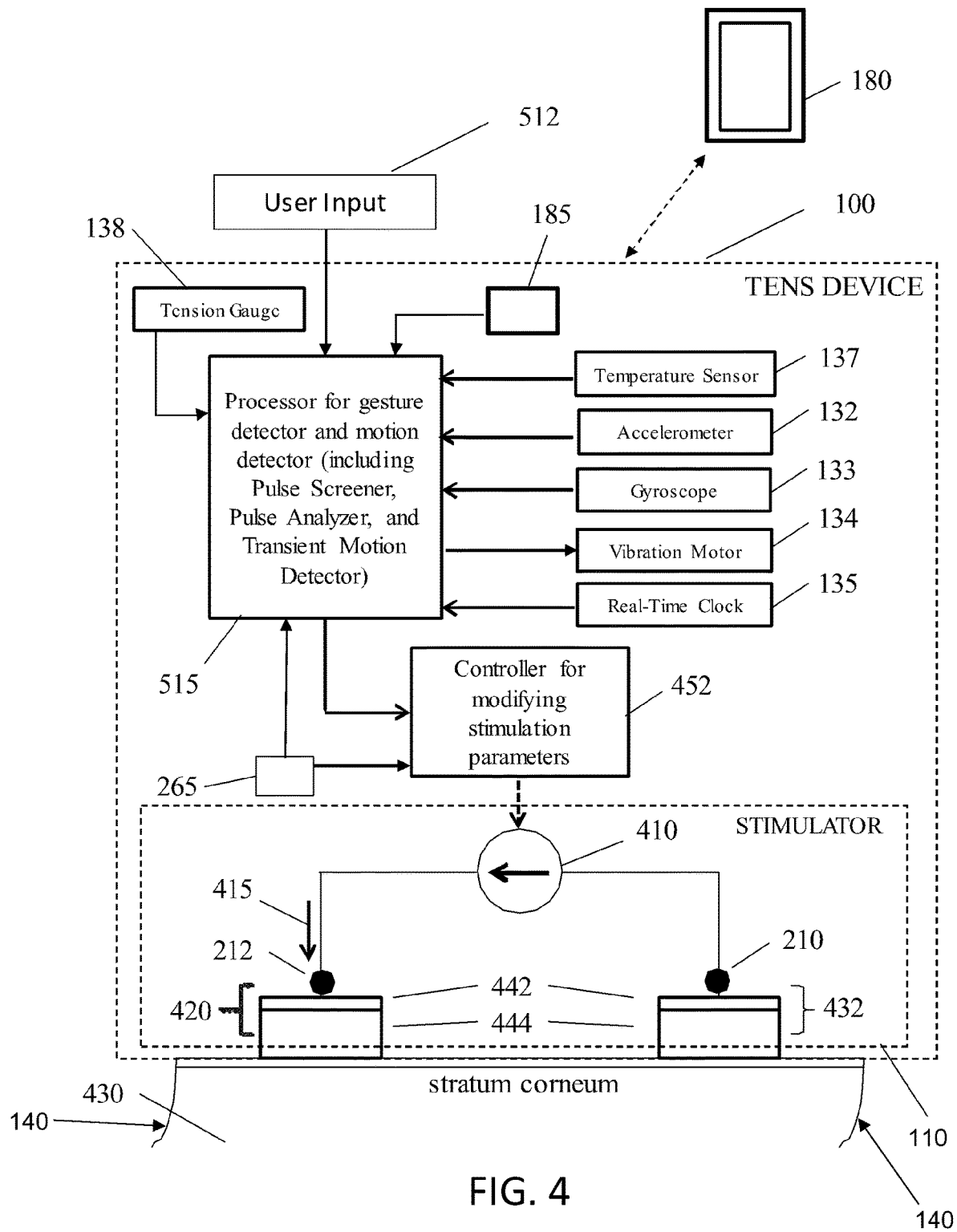
FIG. 4 is a schematic view of the novel TENS device of FIGS. 1-3, including a processor for gesture detection and motion detection (including a pulse screener, pulse analyzer, and transient motion detector)

Note that accelerometer 132 may be located within or outside stimulator housing 111. Accelerometer 132 also monitors motion and orientation of the TENS device when the TENS device is not placed on the body of a user. TENS device 100 also comprises a gyroscope 133 (FIG. 4), a vibration motor 134 (FIG. 4), a real-time clock 135 (FIG. 4), a temperature sensor 137 (FIGS. 2 and 4), and a strap tension gauge 138 (FIGS. 2 and 4). Note that gyroscope 133, temperature sensor 137, and/or vibration motor 134 may be located within or outside stimulator housing 111.

In one preferred form of the invention, stimulator housing 111 also houses a battery (not shown) for powering the TENS stimulation circuitry and other circuitry, and other ancillary elements, such as a wireless link module 185 (FIG. 4) of the sort well known in the art of wireless communications for allowing TENS device 100 to wirelessly communicate with a remote controller 180 (e.g., a hand-held electronic device such as a smartphone or a RFID tag, see FIG. 2).

In another form of the invention, TENS device 100 may comprise more than one stimulator housing 111, e.g., to better conform to the body and/or to improve user comfort by distributing circuitry and battery components more evenly.

And in still another form of the invention, a flexible circuit board is used to distribute the TENS stimulation circuitry and other circuitry more evenly around the leg of the user and thereby reduce the thickness of the device.

Still looking at FIG. 2, user interface element 101 preferably comprises an LED for indicating stimulation status and for providing other feedback to the user. Although a single LED is shown in FIG. 2, user interface element 101 may comprise multiple LEDs with different colors. Additional user interface elements (e.g., an LCD display, audio feedback through a beeper or voice output, haptic devices such as a vibrating element, a smartphone running an appropriate "App", etc.) are also contemplated and are considered to be within the scope of the present invention.

In one preferred form of the invention, TENS device 100 is configured to be worn on the user's upper calf 140 as is shown in FIG. 1, although it should also be appreciated that TENS device 100 may be worn on other anatomical locations, or multiple TENS devices 100 may be worn on various anatomical locations, etc. TENS device 100 (comprising the aforementioned stimulator 110, electrode array 300, and strap 130) is secured to upper calf 140 (or other anatomical location) of the user by placing the apparatus in position against the upper calf (or other anatomical location) and then tightening strap 130. More particularly, in one preferred form of the invention, electrode array 300 is sized and configured so that it will apply appropriate electrical stimulation to the appropriate anatomy of the user regardless of the specific rotational position of TENS device 100 on the leg (or other anatomical location) of the user.

Figure 3:
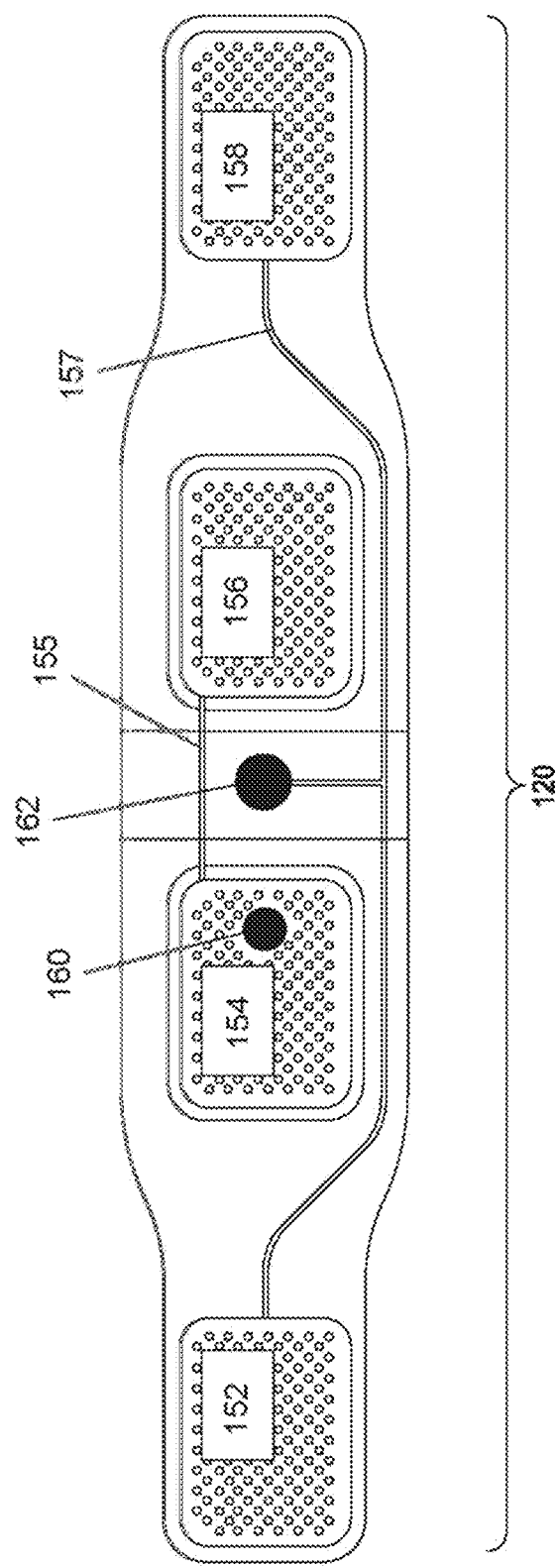
FIG. 3 is a schematic view showing the electrode array of the novel TENS device of FIGS. 1 and 2 in greater detail.

FIG. 3 shows a schematic view of one preferred form of electrode array 300. Electrode array 300 preferably comprises four discrete electrodes 302, 304, 306, 308, each having an equal or similar size (i.e., an equal or similar size surface area). Electrodes 302, 304, 306, 308 are preferably connected in pairs so that electrodes 304 and 306 (representing the cathode of TENS device 100) are electrically connected to one another (e.g., via connector 305), and so that electrodes 302 and 308 (representing the anode of TENS device 100) are electrically connected to one another (e.g., via connector 307). It should be appreciated that electrodes 302, 304, 306, 308 are preferably appropriately sized, and connected in pairs, so as to ensure adequate skin coverage regardless of the rotational position of TENS device 100 (and hence regardless of the rotational position of electrode array 300) on the leg (or other anatomical location) of a user. Furthermore, it should be appreciated that electrodes 302, 304, 306, 308 are not connected in an interleaved fashion, but rather are connected so that the two inside electrodes 304, 306 are connected to one another, and so that the two outside electrodes 302, 308 are connected to one another. This electrode connection pattern ensures that if the two outer electrodes 302, 308 should inadvertently come into contact with one another, an electrical short of the stimulation current flowing directly from cathode to anode will not occur (i.e., the electrode connection pattern ensures that the therapeutic TENS current is always directed through the tissue of the user).

Electrical current (i.e., for therapeutic electrical stimulation to the tissue) is provided to the electrode pairs 304, 306 and 302, 308 by connectors 310, 312 (FIG. 3) which mate with complementary connectors 210, 212 (FIGS. 2 and 4), respectively, on stimulator 110. Stimulator 110 generates electrical currents that are passed through electrodes 304, 306 and electrodes 302, 308 via connectors 310, 312, respectively.

In one preferred form of the present invention, the skin-contacting conductive material of electrodes 302, 304, 306, 308 is a hydrogel material which is "built into" electrodes 302, 304, 306, 308. The function of the hydrogel material on the electrodes is to serve as an interface between the electrodes 302, 304, 306, 308 and the skin of the user (i.e., within, or adjacent to, or proximal to, the portion of the user's body in which the sensory nerves which are to be stimulated reside). Other types of electrodes such as dry electrodes and non-contact stimulation electrodes have also been contemplated and are considered to be within the scope of the present invention.

FIG. 4 is a schematic representation of TENS device 100 and, among other things, the current flow between TENS device 100 and the user. As seen schematically in FIG. 4, stimulation current 415 from a constant current source 410 flows into the user's tissue 430 (e.g., the user's upper calf) via an anode electrode 420 (which anode electrode 420 comprises the aforementioned electrodes 302, 308). Anode electrode 420 comprises a conductive backing (e.g., silver hatch) 442 and hydrogel 444. The current passes through the user's tissue 430 and returns to constant current source 410 through cathode electrode 432 (which cathode electrode 432 comprises the aforementioned electrodes 304, 306). Cathode electrode 432 also comprises a conductive backing 442 and hydrogel 444. Constant current source 410 preferably provides an appropriate biphasic waveform (i.e., biphasic stimulation pulses) of the sort well known in the art of TENS therapy. In this respect it should be appreciated that the designation of "anode" and "cathode" electrodes is purely notational in the context of a biphasic waveform (i.e., when the biphasic stimulation pulse reverses its polarity in its second phase of the biphasic TENS stimulation, current will be flowing into the user's body via "cathode" electrode 432 and out of the user's body via "anode" electrode 420).

Figure 5:
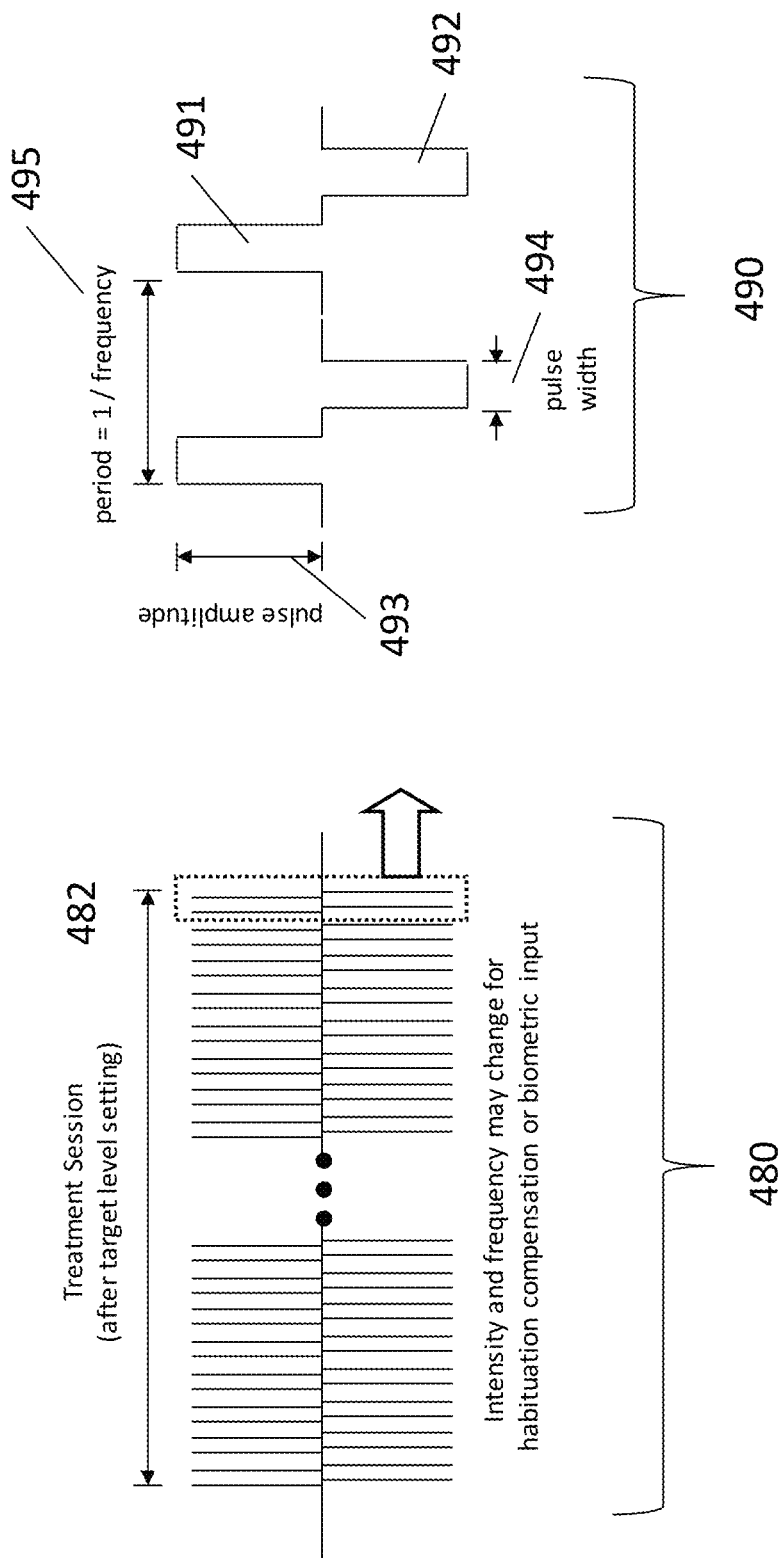
FIG. 5 is a schematic view showing a stimulation pulse train generated by the stimulator of the novel TENS device of FIGS. 1-4.

FIG. 5 is a schematic view showing a pulse train 480 provided by stimulator 110 during a TENS therapy session, and the waveform 490 of two individual biphasic pulses, wherein each individual biphasic pulse comprises a first phase 491 and a second phase 492. In one form of the invention, each pulse waveform is charge-balanced across the two phases 491 and 492 of the biphasic pulse, which prevents iontophoretic build-up under the electrodes of the electrode array 300 that can lead to skin irritation and potential skin damage. In another form of the invention, the individual pulses are unbalanced across the two phases of the biphasic pulse, however, charge-balancing is achieved across multiple consecutive biphasic pulses. Pulses of fixed or randomly-varying frequencies are applied throughout the duration of the therapy session 482. The intensity of the stimulation (i.e., the amplitude 493 of the current delivered by stimulator 110) is adjusted in response to user input and for habituation compensation, as will hereinafter be discussed in further detail.

In prior U.S. patent application Ser. No. 13/678,221, filed Nov. 15, 2012 by Neurometrix, Inc. and Shai N. Gozani et al. for APPARATUS AND METHOD FOR RELIEVING PAIN USING TRANSCUTANEOUS ELECTRICAL NERVE STIMULATION, issued as U.S. Pat. No. 8,948,876 on Feb. 3, 2015, and which patent is hereby incorporated herein by reference, apparatus and methods are disclosed for allowing a user to personalize the TENS therapy stimulation intensity according to the electrotactile perception threshold of the user at the time of the setup of the TENS device. The aforementioned U.S. Pat. No. 8,948,876 also discloses apparatus and methods to automatically restart additional therapy sessions after an initial manual start by the user.

In prior U.S. patent application Ser. No. 14/230,648, filed Mar. 31, 2014 by NeuroMetrix, Inc. and Shai Gozani et al. for DETECTING CUTANEOUS ELECTRODE PEELING USING ELECTRODE-SKIN IMPEDANCE, issued as U.S. Pat. No. 9,474,898 on Oct. 25, 2016, and which patent is hereby incorporated herein by reference, apparatus and methods are disclosed which allow for the safe delivery of TENS therapies at night when the user is asleep. These methods and apparatus allow the TENS device to be worn by a user for an extended period of time, including 24 hours a day.

In order to deliver consistently comfortable and effective pain relief to a user throughout both the day and the night, it may not be appropriate to deliver a fixed TENS stimulation level, since the effect of circadian or other time-varying rhythms can mitigate the effectiveness of TENS stimulation. Parameters impacting TENS stimulation effectiveness include, but are not limited to, stimulation pulse amplitude 493 (FIG. 5) and pulse width 494 (FIG. 5), pulse frequency 495 (FIG. 5), and therapy session duration 482 (FIG. 5). By way of example but not limitation, higher amplitude and longer pulses (i.e., larger pulse charges) increase the stimulation delivered to the user (i.e., the stimulation "dose"), whereas shorter therapy sessions decrease the stimulation delivered to the user (i.e., the stimulation "dose"). Clinical studies suggest that pulse charge (i.e., pulse amplitude and pulse width) and therapy session duration have the greatest impact on the therapeutic stimulation delivered to the user (i.e., the therapeutic stimulation "dose").

For users to gain the full benefit of pain relief throughout both the day and the night from a TENS device, the TENS device should have a low profile for wearability, an easy and intuitive control for usability, and a long-lasting battery life for portability.

Mechanical actuators such as push-buttons and dials increase the physical dimensions of a TENS device. Furthermore, it is difficult to locate and actuate a push-button or dial under clothing unless the push-button or dial is large. However, a large push-button or dial increases the size, thickness, and manufacturing complexity of the device, thereby decreasing its wearability. Moreover, push-buttons and other mechanical actuators are prone to accidental activation such as when the user is sleeping. Therefore, the present invention allows the elimination of mechanical actuators (e.g., push-buttons, dials, etc.) from the TENS device.

Intuitive and easy control enhances the usability of the TENS device. User gestures such as flick, shake, and tap are intuitive ways for a user to interact with their TENS device. The present invention discloses apparatus and methods for processing signals from an on-board accelerometer in order to accurately interpret user gestures.

Extended battery life between charges is a desirable feature for any portable device, especially a TENS device needed for pain relief throughout both the day and the night. However, small total volume and low profile requirements limit the size of rechargeable battery embedded inside a TENS device, and battery capacity is generally related to battery size. Therefore, the capacity of the battery powering the TENS device is thus limited. The present invention discloses apparatus and methods for efficiently managing the power consumption of the TENS device by transitioning the TENS device from an active state to a power-saving state when the TENS device is not in use, and then transitioning the TENS device back to an active state when the TENS device is to be used, all in an intuitive and reliable manner.

TENS Device Operating Mode

In one preferred form of the invention, TENS device 100 operates in one of three modes (see FIG. 6):

(i) an Active mode 176 where TENS device 100 delivers electrical stimulation to the user and maintains an active communication link with remote controller 180;

(ii) a Standby mode 174 where TENS device 100 is ready to start delivering electrical stimulation and maintains an active communication link with remote controller 180; and (iii) a PowerSave mode 172 where TENS device 100 is ready to transition to Standby mode with specific event triggers. Note that it is generally advantageous for TENS device 100 to be in its PowerSave mode whenever possible inasmuch as the Standby mode consumes up to ten times more power than the PowerSave mode.

In PowerSave mode 172, TENS device 100 will turn off all circuitry except for the circuitry of accelerometer 132, which is left active in order to detect gross movement of TENS device 100. The accelerometer circuitry, running a simple motion detection algorithm (e.g., a threshold detector wherein movement is detected when any acceleration signal with an absolute value greater than a threshold value is measured) requires little power for movement detection. Once movement is detected by accelerometer 132, the circuitry of accelerometer 132 sends a signal to the processor 515 (FIG. 4). Upon receiving the signal, processor 515 commands TENS device 100 to enter its Standby mode by turning on its wireless link module 185 and its on-skin detection module 265. In a preferred form of the invention, the circuitry of accelerometer 132 runs at a sampling rate of 50 Hertz for measuring accelerations associated with any movement of the TENS device, inasmuch as the objective is to detect any movement rather than detecting a specific pattern of movement. Running the circuitry of accelerometer 132 at a lower sampling rate can reduce the power consumption of the accelerometer circuitry.

In Standby mode, TENS device 100 activates wireless link module 185, on-skin detector 265, and accelerometer 132. When no "qualified event" occurs within a pre-determined time window, processor 515 returns TENS device 100 to its PowerSave mode. In one form of the invention, the pre-determined time window is 5 minutes. "Qualified events" include communications from/to remote controller 180, specific movement patterns detected by accelerometer 132 (e.g., a tap, a shake, a flick, etc.), and the detection of an on-skin condition. Determination of qualified events is discussed in detail later below. In a preferred form of the invention, processor 515 changes TENS device 100 from its Standby mode to its Active mode by initiating a therapy session after a pre-determined time delay from when the on-skin condition is detected (i.e., the on-skin condition flag transitions from false to true). By way of example but not limitation, the pre-determined time delay may be 20 seconds. In another form of the invention, TENS device 100 remains in its Standby mode as long as an on-skin condition is detected (i.e., the on-skin condition flag is true) and an additional command is needed to initiate a therapy session.

In Active mode, TENS device 100 provides electrical stimulation to the user for a pre-determined period of time and then returns to Standby mode. In a preferred form of the invention, processor 515 starts a timer when TENS device 100 enters its Standby mode from its Active mode, and then automatically initiates the next therapy session at a set time interval if TENS device 100 is still on the skin of the user (i.e., if the on-skin status of TENS device 100 remains true).

If the on-skin condition of TENS device 100 turns false in Active mode, processor 515 will automatically stop electrical stimulation and return the TENS device to Standby mode.

It should be appreciated that processor 515 may comprise a general purpose microprocessor (CPU) of the sort well known in the art together with appropriate programming to provide the functionality disclosed herein, including, among other things, providing the gesture recognition functionality (see below), the tap and flick (pulse) detector functionality (see below), the pulse screener functionality (see below), the pulse analyzer functionality (see below), and the transient motion detector functionality (see below).

On-Skin Detector

In one preferred form of the invention, TENS device 100 comprises on-skin detector 265 (FIG. 4) to confirm that TENS device 100 is firmly seated on the skin of the user.

More particularly, stimulator 110 will automatically initiate an electrical stimulation therapy session after a pre-determined period of delay (e.g., 20 seconds) after the TENS device is secured to the user. In a preferred form of the invention, on-skin detector 265 (FIG. 4) is used to determine whether and when TENS device 100 is securely placed on the skin of the user.

Figure 7:
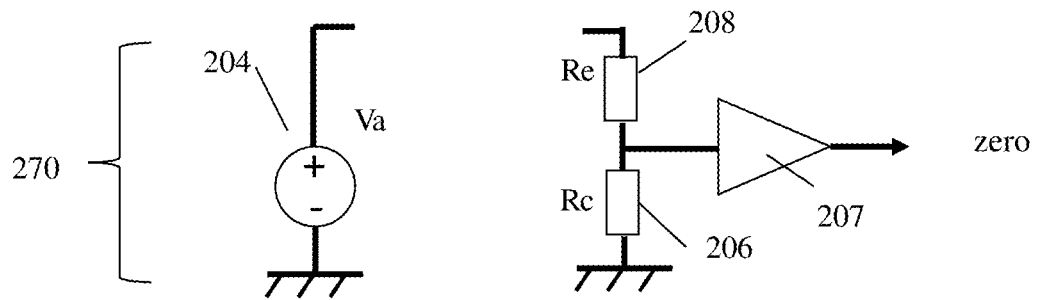
FIG. 7 is a schematic view showing the on-skin detection system of the novel TENS device shown in FIGS. 1-5, as well as its equivalent circuits when the novel TENS device is on and off the skin of a user.
Figure 7:
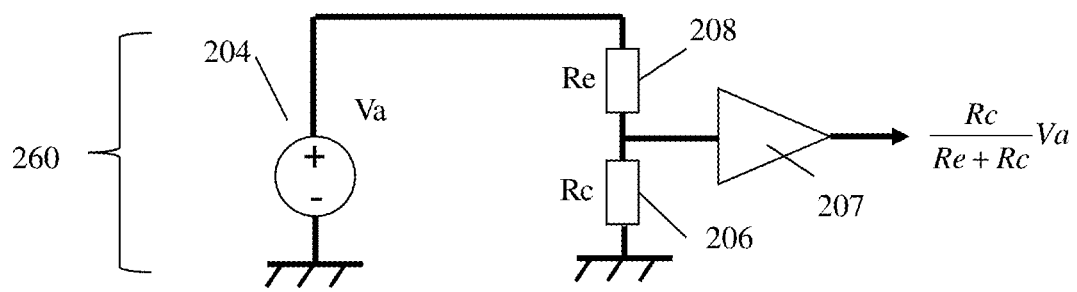
Figure 7:
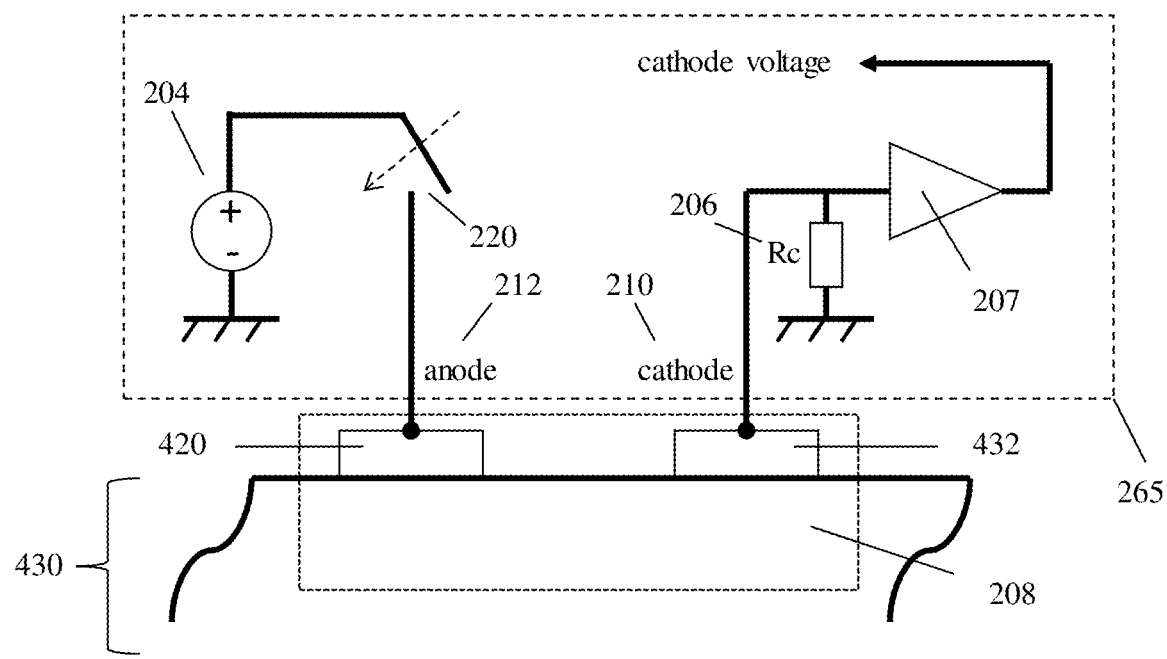

In the preferred form of the invention, and looking now at FIG. 7, on-skin detector 265 is incorporated in TENS device 100. More particularly, in one preferred form of the invention, a voltage of 20 volts from voltage source 204 is applied to anode terminal 212 of TENS stimulator 110 by closing the switch 220. If the TENS device is on the skin of the user, then user tissue 430, interposed between anode electrode 420 and cathode electrode 432, will form a closed circuit to apply the voltage to the voltage divider circuit formed by resistors 208 and 206. More particularly, when TENS device 100 is on the skin of the user, the equivalent circuit 260 shown in FIG. 7 represents the real-world system and equivalent circuit 260 allows the anode voltage $V_a$ 204 to be sensed through the voltage divider resistors 206 and 208. The cathode voltage measured from the amplifier 207 will be non-zero and close to the anode voltage 204 when TENS device 100 is secured to the skin of the user. On the other hand, when TENS device 100 is not secured to the skin of the user, the equivalent circuit 270 (FIG. 7) represents the real-world system and the cathode voltage from amplifier 207 will be zero. When on-skin detector 265 determines that TENS device 100 is on the skin of the user, the on-skin condition is considered to be true, and when on-skin detector 265 determines that TENS device 100 is not on the skin of the user, the on-skin condition is considered to be false. The on-skin condition of TENS device 100 may conveniently be recorded by setting a flag.

On-skin detector 265 is preferably employed in the following way.

If on-skin detector 265 indicates that electrode array 300 of TENS device 100 has become partially or fully detached from the skin of the user, TENS device 100 stops applying TENS therapy to the user and processor 515 of TENS device 100 will transition operation of TENS device 100 from Active mode to Standby mode.

When TENS device 100 is in its Standby mode and on-skin detector 265 determines that the TENS device is not on-skin, the TENS device cannot begin TENS therapy. Therefore, processor 515 disables the user gesture detection for gestures related to TENS therapy such as those gestures for starting and stopping a therapy and those gestures for adjusting therapy intensity (see below). Among the advantages of detecting a smaller set of gestures by processor 515 are: (1) the detection accuracy of fewer candidate gestures will be improved; and (2) the circuitry of accelerometer 132 can be operated at a lower power consumption mode to conserve battery. It is well known in the field of pattern classification that using the same feature sets (from the accelerometer signals) will lead to more accurate classification results (i.e., the features associated with a given signal belong to a target user gesture) if the classification candidate count is reduced. In one preferred form of the invention, the candidate gestures may be reduced to two candidates when TENS device 100 is not on the skin: no gesture at all or any interaction (i.e., gesture) with the TENS device. In this case, accelerometer signals can be sampled at a much lower sampling frequency and a much simpler classification algorithm can be run on the circuitry of accelerometer 132 to detect any gross movement. Both lower sampling frequency and simpler algorithms can lead to lower power consumption by the circuitry of accelerometer 132, and thus provide a longer battery life.

Gesture identification and classification apparatus and methods are described in greater detail below.

Accelerometer Data Sampling

In one preferred form of the invention, a MEMS-based tri-axial accelerometer 132 is mechanically coupled to housing 111 of TENS device 100. The output of accelerometer 132 is electrically coupled with a microcontroller running motion and gesture algorithms (i.e., processor 515).

The gesture algorithms running on processor 515 reliably identify hand gestures (i.e., hand interaction with housing 111 of the TENS device). These hand gestures include a tap to the housing of the TENS device, a double tap to the TENS device (two consecutive taps within a specified time window 630, FIG. 9), and a flick of the TENS device up or down. Additional hand gestures will be apparent to those skilled in the art in view of the present disclosure, and are contemplated and considered to be included within this disclosure.

In one preferred form of the invention, TENS device 100 sets the sampling rate of accelerometer 132 at a rate of 400 Hertz when the TENS device is in its Active mode or its Standby mode and disposed the skin of the user (i.e., its on-skin condition is true, so the TENS device is considered to be on-skin), although a different sampling rate can be utilized. Accelerometer 132 is set to sample at a lower rate (e.g., 100 Hertz) when the TENS device is in Standby mode and not on the skin of the user (i.e., its on-skin condition is false, so the TENS device is considered to be off-skin). The determination of the on-skin or off-skin status of TENS device 100 is accomplished by On-Skin Detector 265 and is discussed in greater detail below. When TENS device 100 is in PowerSave mode, the sampling rate of accelerometer 132 is set at an even lower rate (e.g., 50 Hertz) to further reduce power consumption.

Device Motion Detector

Figure 8:
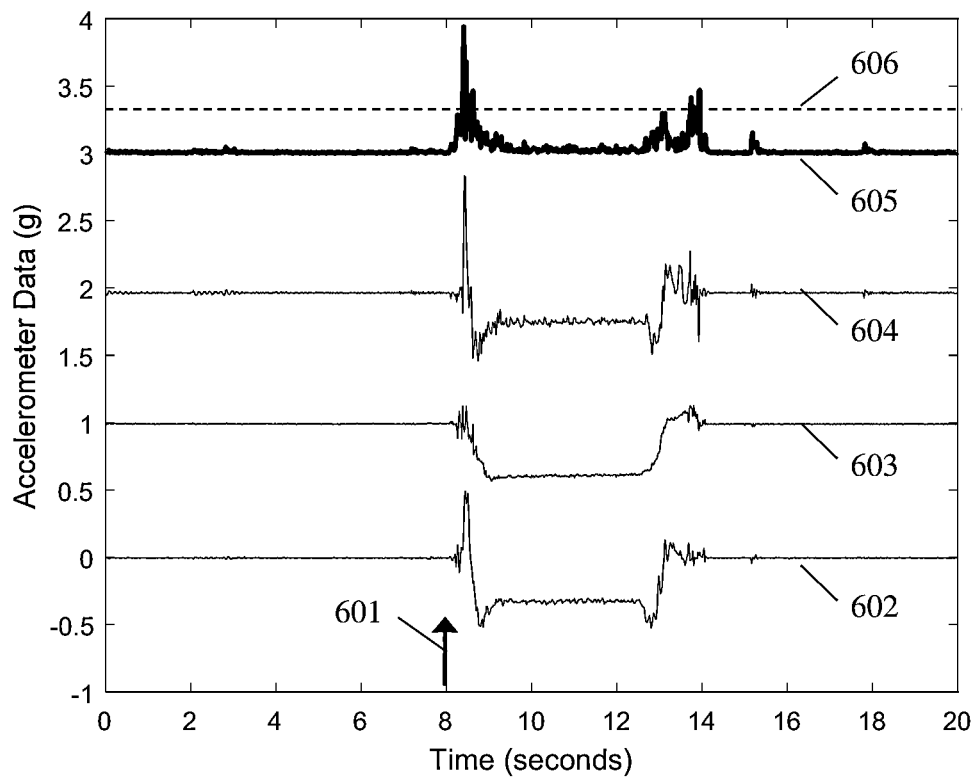
FIG. 8 is a schematic view showing an example of the accelerometer data waveform from the X-, Y-, and Z-axes of an accelerometer incorporated in the novel TENS device, with an additional waveform derived from the accelerometer data for detecting transient motion of the device.

In one preferred form of the invention, accelerometer 132 is sampled at 50 Hertz from all three axes (i.e., the X, Y, and Z directions). A segment of sampled data is shown in FIG. 8. This sampled data was collected where the TENS device initially rested on a flat surface and was then picked up gently at time instance 601. Traces 602, 603, 604 are the accelerometer data from X, Y, and Z directions, respectively. Trace 605 is the summation (over all three axes) of the absolute change of consecutive samples, as defined below:

$$S(t) = \sum_{j=x,y,z} |A_j(t) - A_j(t-1)|$$

where $A_j(t)$ is the accelerometer sample value from the j-axis at the time instance t. A simple threshold detector is sufficient to detect device motion:

$$S(t) > M^{Th}$$

where $M^{Th}$ is a fixed threshold 606. In another form of the invention, the summation of the absolute values of the differences is replaced by the square of the differences. In yet another form of the invention, only data from one axis of the accelerometer is considered. In yet another form of the invention, the threshold 606 is set to be an average of previous samples that have not caused a detected motion event.

Any device motion detected will cause processor 515 of TENS device 100 to transition the mode of the TENS device from PowerSave to Standby. If the TENS device is in Standby mode but not on-skin, the TENS device will return to its PowerSave mode if no further interaction from the user is detected before a countdown timer expires. Interaction from the user may include a command from a connected remote controller 180 or a recognized gesture to start therapy. In one form of the invention, the countdown timer is set to five minutes. If the TENS device is already in Standby mode, a detected device motion will reset the countdown timer to delay the transition from Standby mode to PowerSave mode.

Gesture Recognition

In one preferred form of the invention, control of the operation of TENS device 100 is effected using intentional gestures such as those shown in the table below. The tap gesture is a rapid impact of housing 111 of the TENS device. The flick gesture is a short (small distance) rapid movement of the device up or down. Note that the various gestures are context-sensitive, e.g., a tap in the Standby mode may effect a different change in operation than a tap in the Active mode.

| Gesture | Device Mode | TENS Operation |
|---|---|---|
| Tap | Standby, Off-Skin | Battery Check |
| Tap | Standby, On-Skin | Start Therapy |
| Tap | Active (Therapy) | Halt Therapy |
| Flick Down | Active (Therapy) | Decrease Intensity |
| Flick Up | Active (Therapy) | Increase Intensity |
| Double Tap | Standby, On-Skin | Enter Calibration |
| Tap | Active (Calibration) | Indicate Sensation |

The above context-based gesture control of the operation of the TENS device has the advantage that it is intuitive and easy to learn. Most actions are initiated by a simple tap, and the intensity of stimulation is controlled by a flick wherein the direction (up or down) is associated with the change in intensity (i.e., an up flick is associated with an increase in stimulation intensity and a down flick is associated with a decrease in stimulation intensity). For example, when the TENS device is in Standby mode but not on a user's skin, a tap is interpreted as a battery check command, because therapy or calibration cannot be performed in that condition. When the TENS device is in Standby mode and on-skin, a double tap will cause the device to enter a calibration process. During the calibration process, electrical stimulation will ramp up automatically, and a tap becomes an indication of the user's perception of the stimulation sensation, causing the calibration ramp to stop. When the calibration process is completed, the TENS device returns to Standby mode. When the TENS device is in Standby mode and on-skin, a tap will start therapy stimulation (i.e., the TENS device will enter Active mode). When the TENS device is on the user's skin and the device is in Active mode (i.e., electrical stimulation is occurring), the same tap gesture will stop therapy stimulation and return the device to Standby mode.

In another form of the invention, a gyroscope 133 is mechanically coupled with housing 111 of the TENS device. The lower limb movement patterns can be monitored using gyroscope 133 and "decoded" as control inputs to the TENS device. By way of example but not limitation, a user wearing the TENS device on their lower leg, sitting in a chair and with their feet resting on the floor, can maneuver leg sway in a lateral-medial direction (i.e., left and right) easily and discreetly. Gyroscope 133 can detect the pattern and the number of leg sways occurring within a specific time window (e.g., one second) and use this pattern as a TENS control input. For example, a single leg sway detected by gyroscope 133 can be interpreted as equivalent to a single tap detected by accelerometer 132. Depending upon the operational mode of the TENS device (i.e., PowerSave mode, Standby mode and Active mode), the single leg sway movement can be interpreted differently: the leg sway can cause the stimulation to start if the TENS device is in Standby mode and On-Skin; and the leg sway can cause the stimulation to stop if the TENS device is in Active mode delivering electrical stimulation. A single cycle of back and forth leg sway within a given time period (e.g., one second) can, similarly, be treated as equivalent to a double tap. Continuous back and forth leg sway can be detected and such detection outcome can be treated as a different control command for the TENS device.

In another form of the invention, a combination of data received from gyroscope 133 and accelerometer 132 is used to detect a combination of gesture and leg movements for button-free control of the operation of TENS device 100.

Tap and Flick (Pulse) Detector

In one preferred form of the invention, accelerometer data sampled at 400 Hertz are analyzed to detect certain waveform morphology that corresponds to taps or flicks (collectively, such taps or flicks are referred to herein as pulses). Two taps separated by a time window 630 (FIG. 9) falling within a specified range can be classified as a double tap as a distinct gesture.

Figure 9:
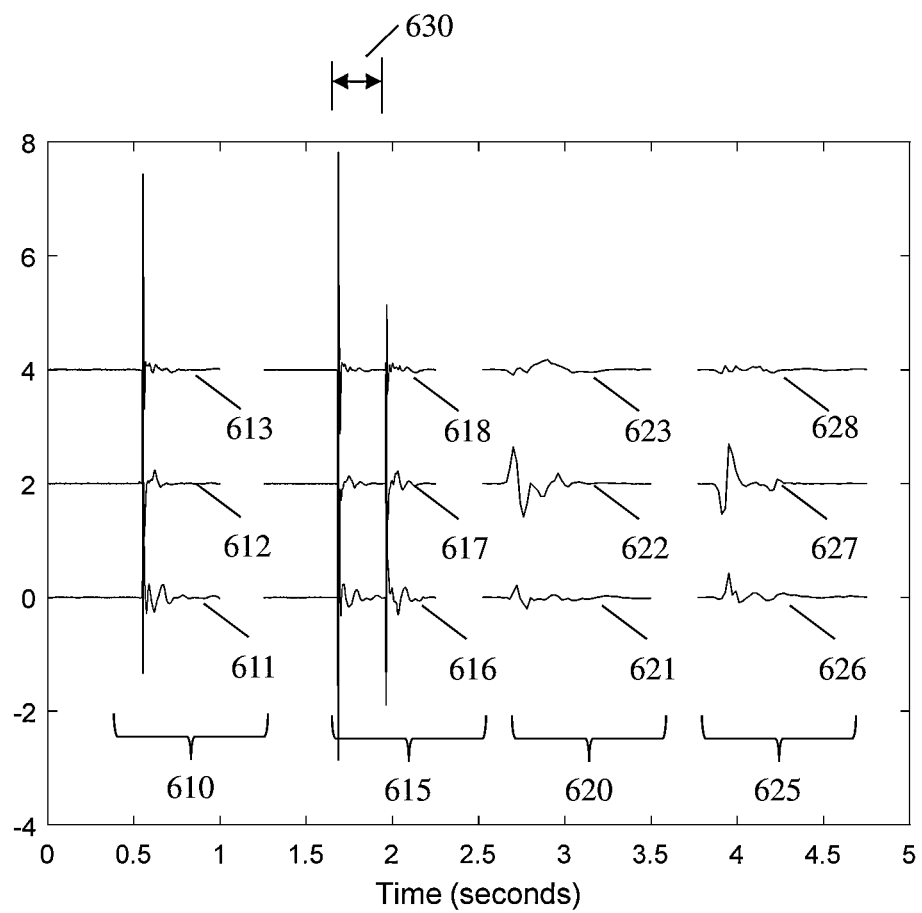
FIG. 9 is a schematic view showing exemplary waveforms from the X-, Y-, and Z-axes of an accelerometer incorporated in the novel TENS device, with the accelerometer data waveform reflecting events associated with tap, double tap, flick up, and flick down.

FIG. 9 shows sample waveforms from the X, Y, Z-axes of an accelerometer mechanically coupled to the housing of a TENS device that is securely strapped on the upper calf of a user. Group 610 corresponds to a single tap gesture, with feature 611 being the accelerometer data from the X-axis, feature 612 being the accelerometer data from the Y-axis, and feature 613 being the accelerometer data from the Z-axis. Group 615 corresponds to a double tap gesture, with feature 616 being the accelerometer data from the X-axis, feature 617 being the accelerometer data from the Y-axis, and feature 618 being the accelerometer data from the Z-axis. Group 620 corresponds to a flick up gesture, with feature 621 being the accelerometer data from the X-axis, feature 622 being the accelerometer data from the Y-axis, and feature 623 being the accelerometer data from the Z-axis. Group 625 corresponds to a flick down gesture, with feature 626 being the accelerometer data from the X-axis, feature 627 being the accelerometer data from the Y-axis, and feature 628 being the accelerometer data from the Z-axis. Note that the accelerometer data for flick up and flick down can be discriminated by examining the polarity of the initial strong peak: a positive peak is associated with a flick up gesture and a negative peak is associated with a flick down gesture.

Figure 10:
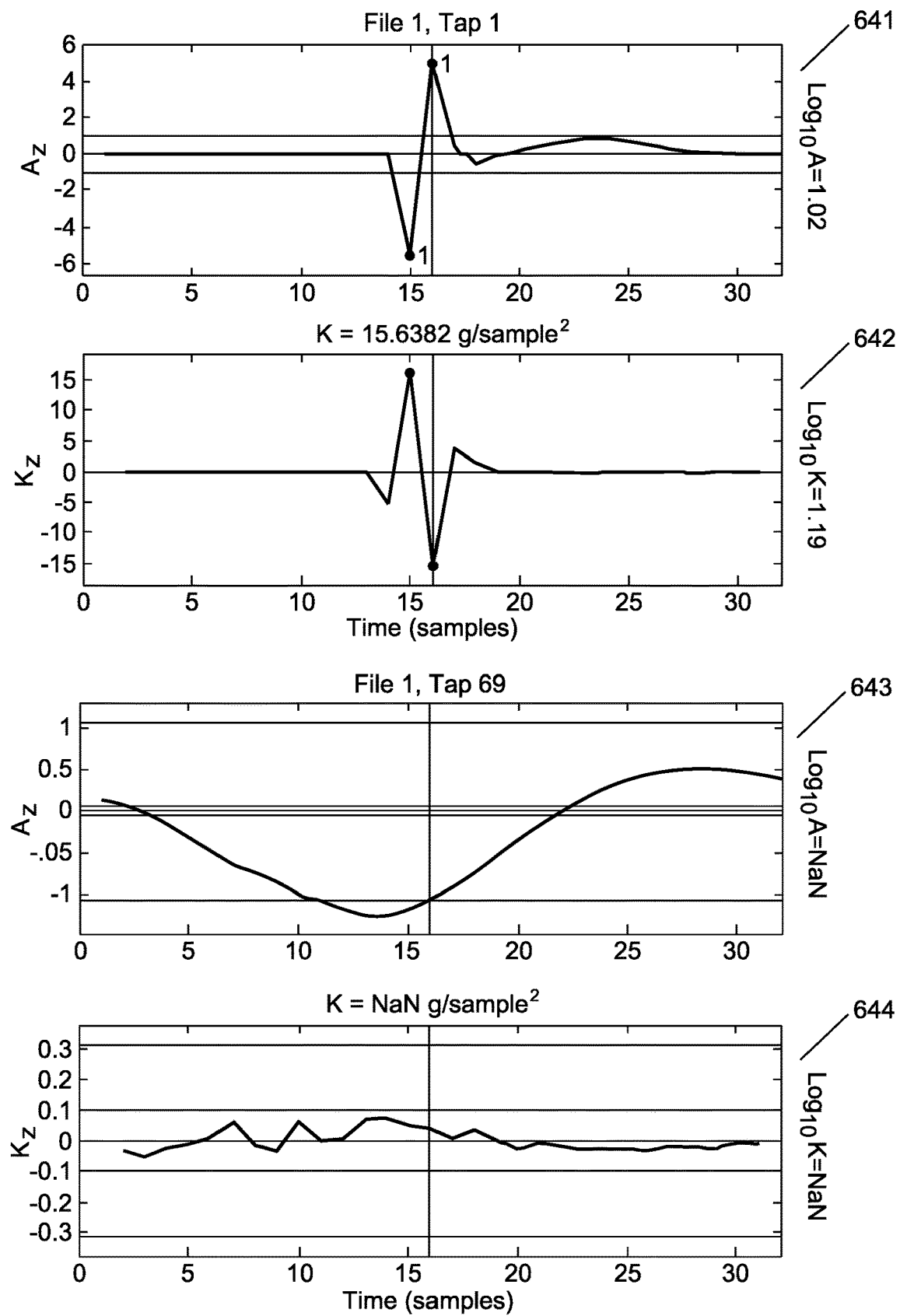
FIG. 10 is a schematic view showing exemplary waveforms from the Z-axis of an accelerometer incorporated in the novel TENS device, with the accelerometer data waveform segments identified by a Pulse Screener as potential pulse events.

The morphology of waveforms associated with a tap or a flick is very similar. A detection algorithm (i.e., a Pulse Detector) can be used to detect both taps and flicks because the accelerometer signals for both taps and flicks share very similar waveform structures. Expanded views of accelerometer signals associated with tap events are shown in FIG. 10 (see 641 and 642). Nevertheless, some distinct characteristics are evident between taps and flicks. A tap has a much larger waveform magnitude than a flick, while the duration of activity is much longer for flicks than for taps. In one preferred form of the invention, one pulse detector is used to detect a tap using one set of parameters (i.e., a shorter pulse duration and a higher pulse amplitude) and the same pulse detector is used to detect a flick using a different set of parameters (i.e., a longer pulse duration and a lower pulse amplitude). In another form of the invention, a dedicated detector is used for tap detection and another dedicated detector is used for flick detection.

In one preferred form of the invention, accelerometer data from the Z-axis are used for tap gesture detection, inasmuch as a user is more likely to tap the TENS device in the Z-axis direction (i.e., perpendicular to the skin) when the device is on-skin (i.e., placed on the upper calf as shown in FIG. 1). Similarly, accelerometer data from the Y-axis are used for flick gesture detection, inasmuch as a user is more likely to flick the TENS device up or down in the Y-axis direction when the device is on-skin (i.e., placed on the upper calf as shown in FIG. 1). In another preferred form of the invention, accelerometer data from all three axes are used for pulse (tap gesture and flick gesture) detection, and a pulse is detected when the waveform morphology from any axis matches a pulse waveform template, whereby to increase pulse detection sensitivity. In another preferred form of the invention, accelerometer data from all three axes are used for pulse (tap gesture and flick gesture) detection and a pulse is detected when the waveform morphologies from all three axes match a pulse waveform template, whereby to improve specificity of pulse detection.

Pulse Screener

In one preferred form of the invention, high-pass filtered accelerometer data, with static gravity removed, are screened by a pulse screener to flag candidate waveform segments. Any waveform from a specified axis whose absolute value exceeds a threshold, then falls back below that threshold within a pre-determined time window, triggers a flag to indicate that waveform segment as a potential pulse. FIG. 10 shows some sample waveform segments that triggered the flag. Waveforms 641 and 642 are associated with valid taps, and waveforms 643 and 644 are not associated with valid taps. Waveform segments flagged by the pulse screener are then analyzed by a Pulse Analyzer (see below) to confirm or to rule out the flagged waveform segment as a valid pulse. In another form of the invention, all waveform segments are analyzed by the Pulse Analyzer to determine the presence of valid pulses.

Pulse Analyzer

In a preferred form of the present invention, 3-axis accelerometer 132 outputs its raw acceleration measurement data at a rate of 400 Hz for each axial direction (i.e., accelerometer 132 reports 400 acceleration measurements per second for the X-axis direction, 400 acceleration measurements per second for the Y-axis direction, and 400 acceleration measurements per second for the Z-axis direction, for a total of 1200 measurements per second). In a preferred form of the invention, only the acceleration data from the Z-axis, $A_z(t)$, are analyzed for the detection of acceleration "pulse" events, i.e., intentional gestures (e.g., taps, slaps, and flicks, etc.) on the TENS device 100 by the user (the Z-axis is sometimes hereinafter referred to as the "primary axis"). In another form of the invention, acceleration data from each of the three axes are analyzed independently for detection of acceleration "pulse" events. In yet another form of the invention, the acceleration data from all three directions are combined into instantaneous acceleration A(t), defined as $$A(t)=\sqrt{A_x(t)^2+A_y(t)^2+A_z(t)^2}$$

and this instantaneous acceleration signal is analyzed for detection of acceleration "pulse" events.

The defining characteristic of an acceleration pulse event (sometimes referred to herein as simply a "pulse"), generated by a tap or similar user gesture, is that acceleration exceeds a threshold (i.e., a positive or negative acceleration threshold), and returns below that threshold within a specified time period (i.e., a time duration threshold). The acceleration data are first high-pass filtered to remove the constant effect of gravity. In a preferred form of the invention, the high-pass filter cut-off frequency is set at 2 Hz in order to remove the effect of gravity while still permitting a range of other uses for the accelerometer data.

Figure 11:
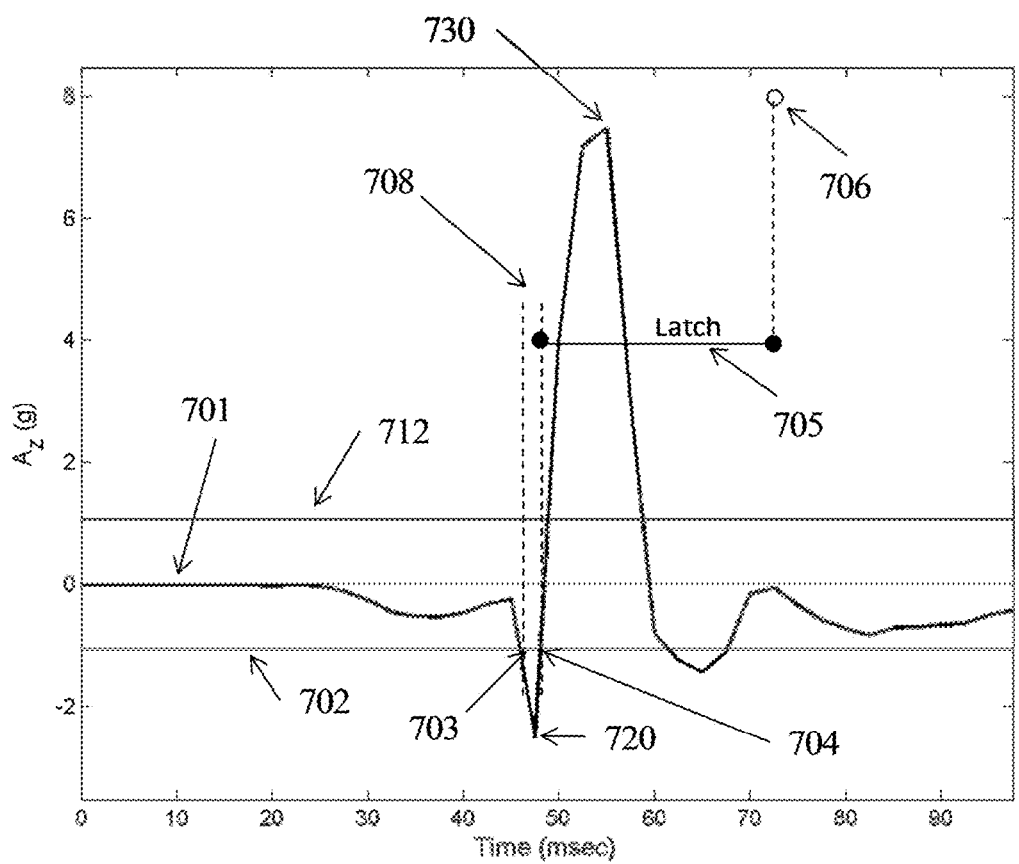
FIG. 11 is a schematic view showing an exemplary waveform from the Z-axis of an accelerometer incorporated in the novel TENS device, wherein the accelerometer data waveform is associated with a tap.

FIG. 11 shows a sample trace 701 of $A_z(t)$ for a "true" tap event (i.e., generated by an intentional user gesture such as a tap) as measured by the accelerometer. Such "true" tap events are sometimes also referred to herein as a "true" acceleration pulse event. Acceleration waveform 701 starts out near zero. When waveform 701 crosses either a positive threshold 712 or a negative threshold 702 (in the instance shown in FIG. 11, it is the negative threshold 702), at time point 703, a timer starts. When waveform 701 crosses the same threshold 702 again, at time point 704, the timer stops. If the timer value (i.e., the time difference 708 between time point 704 and time point 703) is less than a pre-determined duration threshold, then a pulse (also known as an acceleration pulse event) is considered to be detected at time point 704.

For true tap events (i.e., those reflective of an intentional user gesture), the pulse is typically largest and more stereotyped along the primary axis (i.e., along the Z-axis). As a result, in a preferred form of the invention, pulse detection is enabled on only the Z-axis in order to improve detection of true pulse events and limit "false" pulse events (i.e., those not reflective of an intentional user gesture). In another form of the invention, pulse detection is carried out on all three axes. Corresponding threshold values for each axis may be different, depending upon the configuration of TENS device 100. In one form of the invention, a pulse detection outcome is considered to be positive (i.e., a pulse is considered to have been detected) only if the pulse detection in all axis directions under consideration is positive. In another form of the invention, the pulse detection outcome is considered to be positive if the pulse detection in any axis direction under consideration is positive. In yet another form of the invention, the pulse detection outcome is considered to be positive if the pulse detection outcome is positive for a majority of the axes under consideration.

Depending upon the manner in which the user interacts with the TENS device, either the positive or negative peak of the pulse (i.e., the acceleration trace waveform) may be larger and cross detection threshold 702 or 712. In a preferred form of the invention, crossing either positive threshold 712 or negative threshold 702, and returning within the specified time duration period, is considered to constitute the detection of a pulse event. In other words, acceleration peaks lying between threshold 712 and threshold 702 do not constitute a pulse event, and threshold 712 and threshold 702 together effectively form a non-pulse band. A pulse event is detected when the acceleration trace waveform 701 goes outside the non-pulse band briefly for a time duration greater than zero but smaller than the specified time duration period. In one preferred form of the invention, both thresholds (i.e., thresholds 702 and 712) may have the same magnitude or absolute value. In another form of the invention, positive threshold 712 is larger than negative threshold 702 (in absolute value), effectively requiring that the pulse waveform have a larger positive peak in order to be recognized as a pulse event. In yet another form of the invention, positive threshold 712 is set to a very large number, exceeding the largest possible measured acceleration value. Setting positive threshold 712 to such a very large number effectively causes pulse detector 515 to ignore the positive pulse peak and requires the pulse waveform to have negative polarity (i.e., a negative peak with an amplitude exceeding threshold 702) in order to constitute a pulse event.

Thus it will be seen that the pulse detector (an algorithm implemented by processor 515) utilizes a pulse detection algorithm that has two main parameters: positive and negative amplitude thresholds (measured in units g, standard gravity acceleration), and a time duration threshold (measured in units msec). In a preferred form of the invention, the amplitude threshold values and the time duration threshold values are fixed values which are derived experimentally, e.g., from a population study. Based on one population study, the parameters are set as follows: positive amplitude threshold: +1 g, negative amplitude threshold: −1 g, and time duration threshold: 15 msec. In another form of the invention, the amplitude threshold values and the time duration threshold value are adapted to the behavior of an individual user. For example, if a stronger pulse waveform always follows a weaker pulse waveform (i.e., the weaker pulse waveform just misses the threshold value 702 and the stronger pulse waveform exceeds the threshold 702), threshold value 702 may be reduced (in absolute value) to allow pulse detector 515 to correctly recognize a weaker tap as a "true" acceleration pulse event (and hence an intentional user gesture). Similar process may be used for adaptation and differentiation of the threshold values in different axes. As discussed above, the same processor 515 can be used to detect a flick pulse, with a lower amplitude threshold (e.g., >0.3 g) and time duration range between 25 ms and 75 ms.

Figure 12:
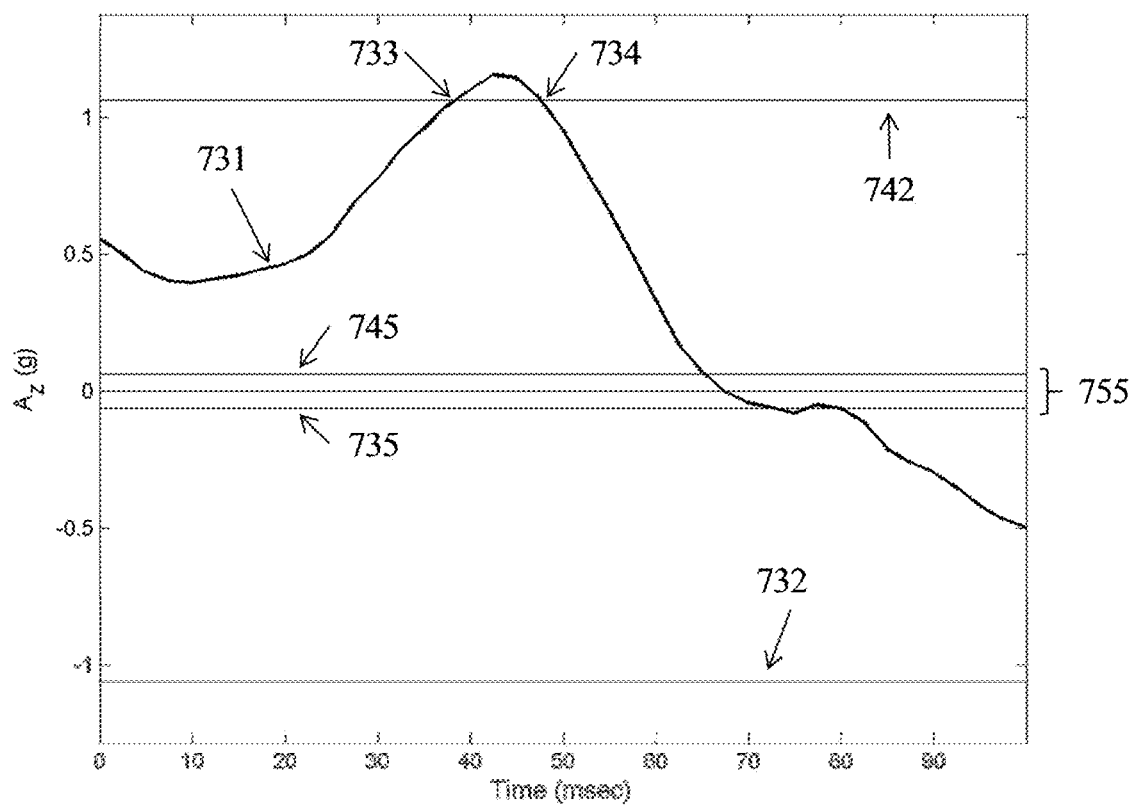
FIG. 12 is a schematic view showing an exemplary waveform from the Z-axis of an accelerometer incorporated in the novel TENS device, wherein the accelerometer data waveform is associated with walking activity.

FIG. 12 shows an example of a "false" pulse event caused by walking. More particularly, in this example, the acceleration waveform 731 crosses the positive threshold 742 at time 733, and returns below positive threshold 742 at time 734. In contrast to a "true" acceleration pulse event like that shown in FIG. 11 (where the acceleration trace remains close to zero prior to the occurrence of a "true" acceleration pulse event), in the "false" pulse event of FIG. 12 the acceleration waveform 731 prior to time 733 is consistently displaced from zero, as is typical during normal user behaviors like walking. FIG. 12 also shows a second set of thresholds (735 and 745), called transient motion thresholds, which are much smaller than the aforementioned pulse thresholds 732 and 742. The acceleration values between threshold values 735 and 745 form a non-transient motion region 755. A "false" acceleration pulse event tends to have accelerations that exceed these smaller thresholds 735 and 745 (i.e., outside the non-transient motion region 755) prior to pulse detection: this fact is used (see below) to preclude trace 731 in FIG. 12 from being classified as a "true" acceleration pulse event.

Transient Motion Detector

Figure 13:
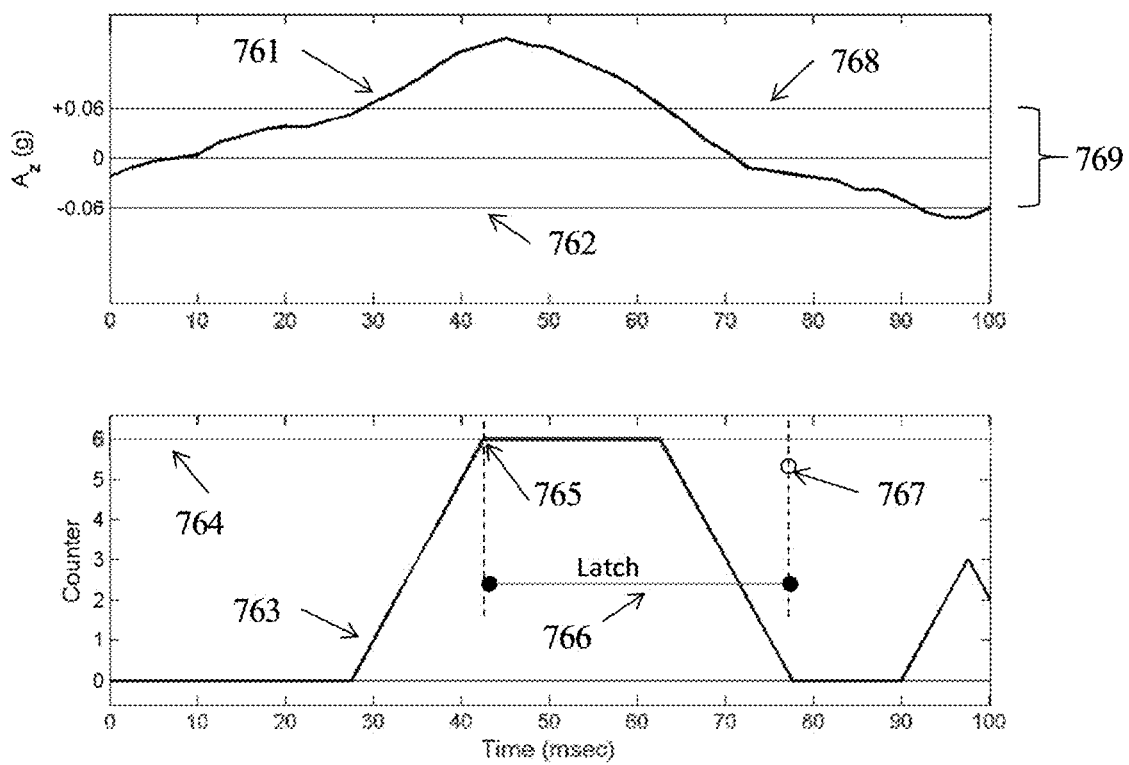
FIG. 13 is a schematic view showing an exemplary waveform from the Z-axis of an accelerometer and an activity counter to assess transient activities.

Processor 515 of TENS device 100 comprises a transient motion detector for detecting transient motion during walking, etc. The defining feature of transient motion is that the high-pass filtered acceleration waveform exceeds some amplitude threshold, and remains above that amplitude threshold, for at least some time duration. More particularly, FIG. 13 shows a segment of an acceleration waveform 761 corresponding to transient motion during walking, etc. When acceleration waveform 761 is above a transient motion threshold 768 or below a transient motion threshold 762, a counter 763 increments with each time sample taken along trace 761, otherwise counter 763 decrements. In other words, counter 763 increments by one for each sample time if the waveform sample of the acceleration waveform 761 stays outside a non-transient motion region 769 bounded by thresholds 762 and 768; otherwise counter 763 decrements by one for each waveform sample that falls inside the non-transient motion region 769. The value of counter 763 is bounded between 0 and a specified counter threshold value 764 (e.g., an exemplary counter threshold value of 6 in FIG. 13). Any time counter value 763 is equal to threshold counter value 764, a flag (e.g., in the microprocessor of processor 515) is set to indicate the occurrence of transient motion. With appropriate transient motion threshold 762 and 768, and an appropriate counter threshold value 764, the transient motion detection algorithm utilized by the transient motion detector of processor 515 can detect body movements of the user due to walking and other normal activities. In a preferred form of the invention, to maximize the detection of transient motion events, transient motion detection is enabled for all three axes (i.e., acceleration is detected, and the acceleration data utilized, for all three axes). In another form of the invention, transient motion detection is only enabled for axis directions found to optimize performance of the transient motion detector of processor 515.

The transient motion detection algorithm utilized by the transient motion detector of processor 515 utilizes three main parameters: positive and negative amplitude thresholds (measured in units g), and duration threshold (measured in units msec). In a preferred form of the invention, the duration threshold is converted to an equivalent discrete sample counter value for a discretely sampled waveform. In a preferred form of the invention, positive and negative amplitude threshold values, and the counter threshold value, are fixed values which are derived experimentally, e.g., from a population study. Based on one population study, the parameters are preferably set as follows: positive amplitude threshold: +0.0625 g, negative amplitude threshold: −0.0625 g, and duration threshold: 15 msec (which corresponds to a counter threshold equal to 6 for waveforms sampled at 400 Hz). In another form of the invention, positive and negative amplitude threshold values, and the counter threshold value, are adapted to an individual user's behavior.

Integration of Transient Motion Detector and Pulse Analyzer: Pulse Detector

When a user intentionally taps TENS device 100, an acceleration pulse event (or "pulse event") is created which is readily identified by the aforementioned pulse detection algorithm utilized by the pulse detector of processor 515 (i.e., the pulse detector is designed to have high sensitivity so as to ensure reliable detection of the acceleration pulse event). However, pulse events must correspond to actual tap events initiated by the user in order for the gesture control to be of practical value, i.e., the overall system must have high specificity. Inasmuch as transient motion such as walking can lead to "false" pulse events, these "false" pulse events must be identified and rejected without reducing the sensitivity to "true" pulse events (i.e., those reflecting intentional user gestures). Because the underlying cause of "false" pulse events is transient body motion, the present invention detects transient motion due to walking and other normal body movements, and rejects pulse events in close temporal proximity to transient motion. In other words, the pulse detection algorithm of the pulse detector of processor 515 must be sensitive so that it does not miss the detection of "true" pulse events caused by intentional user gestures (e.g., taps by the user on TENS device 100), but the TENS device must also be capable of discerning "false" pulse events caused by walking and other normal body movements and rejecting such "false" pulse events as being unrelated to intentional user gestures.

The temporal proximity of transient motion and acceleration pulse events provides a reliable means for discriminating between "true" acceleration pulse events corresponding to actual user gestures (e.g., taps on TENS device 100), and "false" acceleration pulse events caused by transient motion due to walking and other normal body movement. An important aspect of the present invention lies in this recognition and the determination of such temporal proximity.

Pulse events have sharp initial deflections lasting 10-20 msec, followed by decaying oscillations lasting 50-100 msec. Thus, even "true" pulse events (i.e., those reflective of an intentional user gesture) generate transient motion events immediately after the "true" pulse event. Therefore, in a preferred form of the invention, transient motion events immediately following pulse events are ignored for purposes of discriminating between "true" pulse events and "false" pulse events. However, transient motion events temporally separated from pulse events are used to discriminate between "true" pulse events and "false" pulse events.

Figure 14:
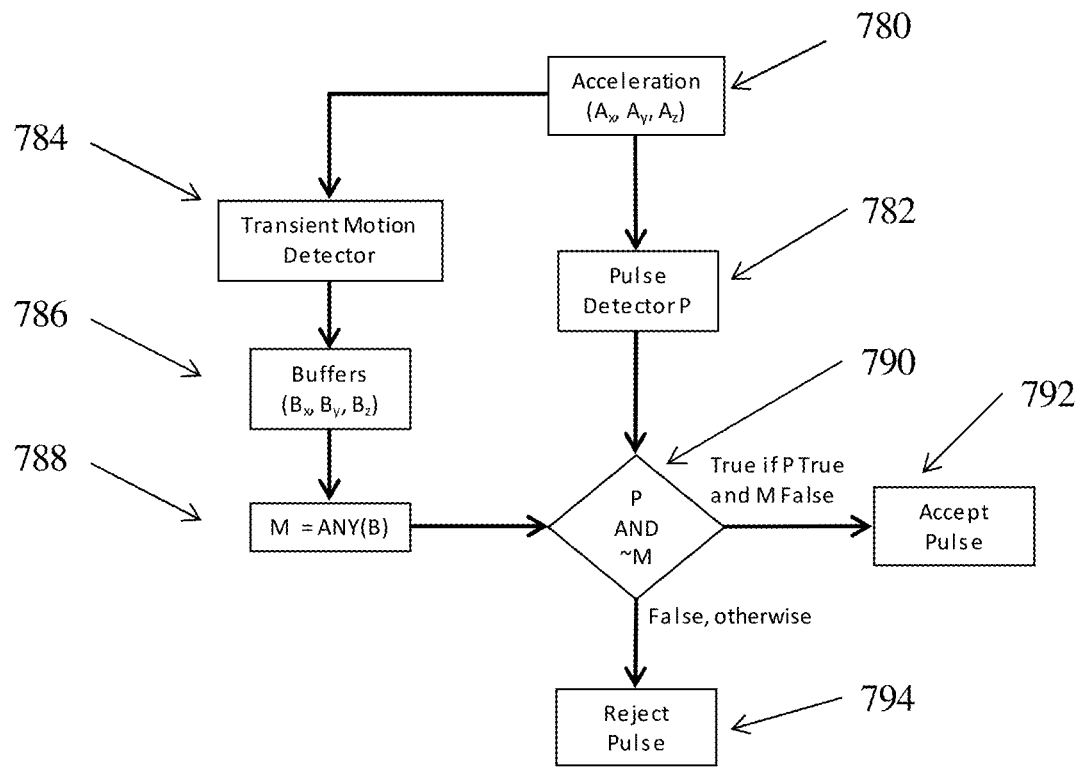
FIG. 14 is a flowchart showing how transient motion events can be used to discriminate between "true" acceleration pulse events representative of intended user gestures and "false" pulse events representative of ordinary body movements.

More particularly, FIG. 14 shows a flowchart for a preferred form of the present invention. The acquired acceleration data (block 780) from each axis ($A_x(t)$, $A_y(t)$, $A_z(t)$) are processed individually by the transient motion detector algorithm of processor 515 (block 784) to detect transient motion as described above. Detected transient motion events are stored in a buffer (block 786) for each axis ($B_x$, $B_y$, $B_z$). The buffer contents are updated to include only events detected in the most recent time period (e.g., in the most recent 150 msec). If any of the buffers is "true" (i.e., reflecting a detected transient motion event), then processor 515 sets a transient motion flag M to "true" (block 788); otherwise, the transient motion flag M is set to "false".

The acceleration data 780 from the primary axis direction ($A_z(t)$) are processed by the pulse detector algorithm of processor 515 (block 782). The current pulse detection result P, and a history of transient motion detection results (summarized by flag M), are analyzed by the processor 515 (block 790). When a pulse is detected (i.e., pulse detect flag P is "true"), if transient motion is absent (i.e., if transient motion flag M is "false"), then processor 515 accepts the pulse event as a "true" pulse event (block 792) which is reflective of an intentional user gesture, otherwise processor 515 rejects the pulse event as a "false" pulse event (block 794).

The temporal proximity of transient motion and acceleration pulse events provides the means for discriminating between "true" acceleration pulse events corresponding to actual user gestures (e.g., taps on TENS device 100), and "false" acceleration pulse events caused by transient motion due to walking and other normal body movement. The duration of the buffers (block 786) sets the degree of temporal proximity required between transient motion events and acceleration pulse events when discriminating between "true" acceleration pulse events and "false" acceleration pulse events.

In a preferred form of the invention, the duration of the buffers (block 786) is determined by an optimization procedure based upon data acquired from users wearing the device.

One key factor in this optimization is the following. By the laws of physics, and specifically the laws of kinematics, linear displacement of an object from one relatively stationary state to another relatively stationary state involves acceleration in one direction (initiation of movement) followed by acceleration in the opposite direction (cessation of movement). Accelerometer data from a pulse, like that shown in FIG. 11, shows two prominent peaks 720 and 730 consistent with this physical understanding. A sample rate of 400 Hz is fast enough to capture these peaks, but different examples of pulse waveforms have different relative peak sizes, presumably because the accelerometer samples have effectively random temporal alignments with respect to the actual physical peaks. In FIG. 11, the negative peak 720 was followed by a positive peak 730 that happens to be larger. The negative peak 720 crosses the negative threshold 702, and results in the detection of the pulse at time 703 based on that negative peak. Depending upon the overall shape of the pulse waveform 701 and the negative threshold 702, however, the first peak 720 may not result in pulse detection. Depending upon the size of the second peak 730 and the positive threshold 712, it may be the second peak that results in pulse detection. In such a case, even though the first peak 720 did not result in pulse detection, it may cross the transient motion detection threshold 762 (FIG. 13) and, depending upon the acceleration profile and transient motion duration threshold, it may result in the detection of transient motion. In a preferred form of the invention, therefore, the transient motion buffers 786 span a time interval that excludes an interval (0-50 milliseconds) immediately preceding a detected pulse. In a preferred form of the invention, these buffers cover a time interval of 50-150 milliseconds before a detected pulse. Other values of these parameters have been contemplated and are considered to be within the scope of the present invention.

Remote Controller

TENS device 100 can also be controlled by a remote controller 180. Examples of such a remote controller include an App running on a Bluetooth-enabled smartphone, a finger ring with a RFID (radio frequency identification) tag, a bracelet with an RFID tag, etc. Operation of TENS device 100 can be controlled directly by commands sent to TENS device 100 via a secure wireless link from remote controller 180 to the TENS device. Remote controller 180 can also serve to supplement other schemes for controlling TENS device 100, or to modify other schemes for controlling TENS device 100, e.g., the aforementioned gesture control. By way of example but not limitation, TENS device 100 can be configured to allow a tap gesture to be detected more readily (i.e., for threshold parameters to be relaxed) if an RFID ring or bracelet is detected near the TENS device.

Radio Frequency Identification (RFID) Tag

Radio Frequency Identification (RFID) uses electromagnetic fields to transmit electronically-stored information remotely to a nearby RFID reader. Two types of RFID tags are generally available: passive and active. Passive RFID tags collect energy from the probing radio waves of a nearby RFID reader and use that energy to transmit signals from the RFID tag to the RFID reader. Active RFID tags have a local power source (e.g., a battery) to transmit stored information for up to several hundreds of meters.

In one preferred form of the invention, a passive RFID tag is embedded in a ring to be worn on a user's finger. An RFID reader is embedded in the TENS device. When the RFID ring (i.e., the remote controller 180) is placed close to the TENS device, the RFID reader and the RFID tag exchange appropriate security information. After the RFID tag is validated to determine that information from this RFID tag (i.e., the ring worn on the user's finger) is intended for the TENS device, information from the RFID ring (i.e., remote controller 180) is transmitted to TENS device 100. This transmission is received by wireless link module 185 of TENS device 100 and is then interpreted by TENS device 100.

In one preferred form of the invention, information from the RFID ring (i.e., remote controller 180) is used to start therapy when the TENS device is in Standby mode 174 and the on-skin status condition is "true". Similarly, information from the RFID ring is used to stop therapy (i.e., to stop electrical stimulation) when the TENS device is in Active mode 176 (i.e., delivering therapeutic stimulation pulses to the user).

Figure 6:
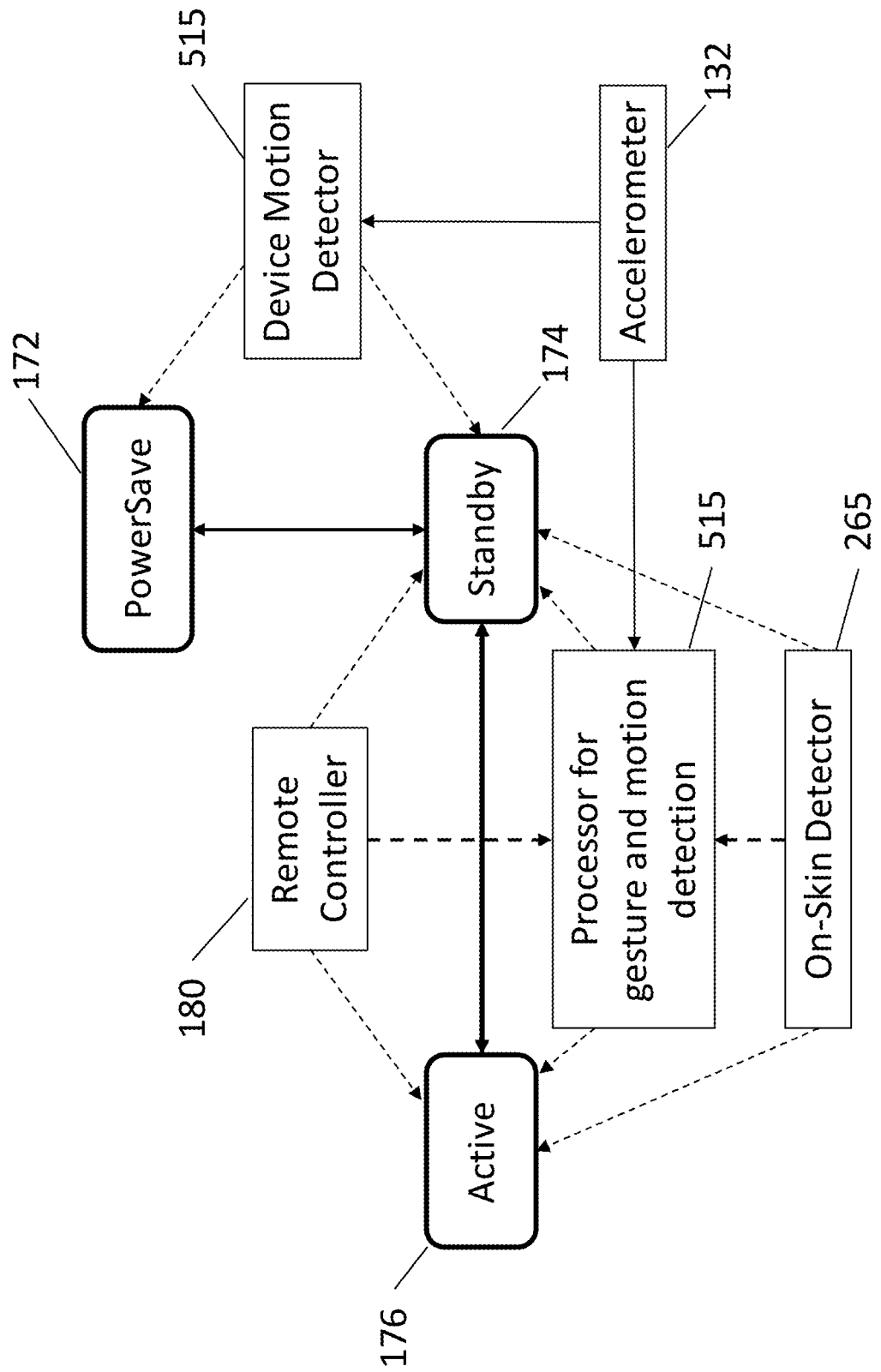
FIG. 6 is a schematic view of showing various operating modes (PowerSave, Standby, and Active) of the novel TENS device shown in FIGS. 1-5, and the transitions between the modes of operation.

In another preferred form of the invention, the presence of a validated RFID ring modifies the behavior of the Pulse Detector of processor 515 so as to improve the responsiveness of the TENS device to user gestures (see FIG. 6). Recall that transient motion is used to block certain pulses detected by the Pulse Analyzer of processor 515 as body movement (e.g., walking) may cause the accelerometer to generate a waveform similar to that of a gesture. However, when an RFID ring (i.e., remote controller 180) is detected near TENS device 100, it is more likely that pulse-like motion sensed by the accelerometer is indeed generated by an intended gesture from the user. Thus, processor 515 can be configured so that the presence of the RFID ring will reduce the likelihood of rejecting a valid pulse due to transient motion, whereby to make the TENS device more responsive to an intentional user gesture when the hand with the RFID ring is detected near the TENS device.

RFID ring can be used to customize the Pulse Analyzer of processor 515 to individual gesture patterns so as to improve its performance. By way of further example but not limitation, each person has a different preferred pace for a double tap (i.e., the time delay between two taps intended to be a double tap, 630 in FIG. 9). Similarly, the amount of force each person will use to perform a tap gesture may differ. Initially, the Pulse Analyzer of processor 515 may set the double tap delay 630, and accelerometer signal thresholds 702 and 712, to threshold values optimized for most users. It is well known in the field of machine learning that the quality of training data determines the rate of learning. In other words, high quality training data with little or no noise should be used to modify existing classification rules more aggressively, while training data with poor quality (high noise) should be used conservatively to modify existing classification rules. The presence of an RFID ring provides an indication that training data quality is good, so that the Pulse Analyzer of processor 515 can be adapted to specific gesture patterns of the user with fewer training samples. If more than one user shares the same TENS device, the unique RFID ring of each user will serve as an indicator of which user is attempting to interact with the TENS device. As a result, the Pulse Analyzer of processor 515 may be customized to each individual user based upon the detected RFID ring. Pulse Analyzer customization may take the form of just a parameter update, or it may take the form of a different way of analyzing the accelerometer waveforms.

In addition to being used to customize operation of the Pulse Analyzer of processor 515, the RFID ring can also be used to customize other aspects of the TENS device. By way of further example but not limitation, each person has their own preferred TENS therapy profile, including stimulation intensity (stimulation pulse amplitude 493) and stimulation pulse patterns (such as pulse frequency 495, therapy session duration 482, and intervals between consecutive therapy sessions). A TENS device may store multiple therapy profiles, and the profile specific to an individual may be loaded into controller 452 once the information necessary to identify the TENS user is detected from the user's RFID ring. Other customization schemes may include a RFID ring (or other RFID tag) disposed by the bed of the user to automatically transition the TENS device into a nighttime therapy profile (if the user has different stimulation preferences for day and night).

In another form of the invention, a passive RFID tag is embedded in a bracelet worn by the TENS user, or in a key chain carried by the user, etc. RFID tags can also be installed at the entrance(s) to the user's home (or office) to allow the user's TENS therapy profile to toggle between indoor (less active or nighttime) and outdoor (more active or daytime) therapy profiles.

Exemplary Operation

In one preferred form of the invention, TENS device 100 comprises a stimulator 110, a strap 130 with a pocket 112 to hold the housing 111 of the stimulator, and an electrode array 300 that connects to the stimulator (both electrically and mechanically) via connectors 210 and 212. Processor 515 for gesture detection and motion detection is preferably disposed in housing 111 of stimulator 110. Strap 130 allows the TENS device to be placed securely on a user's upper calf 140 in order to provide pain relieving therapy with electrical stimulation pulses.

When TENS device 100 is not placed on the skin, the TENS device (and, more specifically, stimulator housing 111) is typically placed on a stationary surface such as a desktop. If TENS device 100 detects no movement and no active communications from or to a remote controller 180 within a set period of time (e.g., five minutes), the TENS device automatically goes into its PowerSave mode 172. In the PowerSave mode, accelerometer 132 is running at a low power mode for detecting only gross movement based on data sampled at 50 Hertz. The wireless link module 185 will also be turned off to conserve energy in the PowerSave mode.

When a user is ready to use the TENS device, the user will first pick up the TENS device 100. Processor 515 will detect the device motion and transition the TENS device into Standby mode 174. In this Standby mode, the TENS device turns on its wireless link module 185 so that communications with one or more remote controllers 180 can be established or re-established. A single tap on the stimulator housing (acting as User Input 512, see FIG. 4) serves as a battery check gesture command. Upon recognizing the battery check gesture command, the TENS device displays the battery level to the user via User Interface Element 101 (e.g., by activating an LED).

Through wireless link module 185, a smartphone App (running on remote controller 180) can be used to control operation of the TENS device, e.g., to customize device setup and user preference. Similarly, an RFID tag (such as in the form of an RFID ring) can be used to trigger the TENS device to load an appropriate device setup for the user when the user places the RFID ring close to the TENS device. The RFID tag can be pre-programmed by the user or by the user's caregivers.

When the TENS device is in Standby mode, it will also enable on-skin detection module 265. On-skin detection generally only requires a voltage setting of 20 volts (rather than 100 volts as is required when the TENS device is in Active mode and therapeutic stimulation is required). On-skin detection module 265 sets the on-skin status to "true" once the TENS device is placed on the skin. Before the on-skin status turns true, the accelerometer sampling rate is increased to 100 Hertz (from its PowerSave mode of 50 Hertz) so as to detect gross user gestures (but it does not yet need to be increased to its Active mode 400 Hertz sampling rate inasmuch as valid user gestures are limited at this point). If the on-skin status is not "true" and no further actions (including recognized gesture, active communications from remote controller, and device motion) are detected from the user for five minutes, the TENS device will automatically return to its PowerSave mode.

If the on-skin status is set to true when the TENS device is in its Standby mode, the TENS device will stay in Standby mode 174 until the on-skin status is changed to false or until the TENS device transitions to its Active mode 176. Transition from the Standby mode to the Active mode can be triggered by a command from a remote controller 180 (such as an App running on a smartphone) or by a gesture recognized by processor 515. Under default conditions, Processor 515 sets parameters for recognizing "Start Therapy" gesture (single tap) in a way to ensure high specificity, that is, only the true intended gesture will be recognized to minimize the chance that other activities such as walking are being incorrectly classified as tap. Unintentional start of TENS therapy is undesirable as it may startle the user. However, if a recognized RFID ring is nearby when gesture-like accelerometer data are recorded, processor 515 may "more aggressively" recognize the gesture movement as a single tap as the proximity of the ring is a reliable indication that the user intended to interact with the TENS device by placing his/her hand (with the RFID ring) close to the TENS device.

Instead of a single tap, a user may use a double tap gesture to initiate a calibration process when the TENS device is on-skin. During the calibration process, the stimulation intensity gradually ramps up from an intensity below the electro-tactile sensation threshold. Using a single tap, the user can indicate their sensation threshold to the TENS device when the stimulation intensity rises high enough to cause a sensation of the electrical stimulation. Once the user indicates that the stimulation intensity has risen high enough to cause a sensation of the electrical stimulation (i.e., by providing the user gesture tap), the intensity ramp is stopped.

Assuming that processor 515 is programmed to recognize two single taps with a time delay between 0.3 and 0.6 seconds, if all previously-recognized double taps from this user have a time delay of between 0.3 and 0.4 seconds, processor 515 can update its double tap time delay range to 0.25 to 0.45 seconds to further improve its gesture recognition accuracy.

When TENS device 100 is in its Active mode, it delivers electrical current pulses at an intensity proportional to the user's electro-tactile sensation threshold. The user may wish to adjust the stimulation intensity from time to time. This can be accomplished via a remote controller 180 such as a smartphone App. Pre-programmed RFID tags can also be used to accomplish the same: the user may hold one RFID tag close to the TENS device to increase stimulation intensity and use a different tag for decreasing stimulation intensity.

Gestures like flick up or flick down can also be employed to control the stimulation intensity. Processor 515 is preferably configured to detect a single tap from Z-axis accelerometer data and a flick up or a flick down from Y-axis data. As shown in FIG. 9, the waveform associated with a tap gesture has a higher amplitude and shorter duration than the amplitude and duration features of a waveform associated with a flick. The same classification algorithm can be used by processor 515 to identify tap and flick gestures. Based on their amplitude and duration features, tap and flick can be differentiated from each other. Once a flick is identified, the initial peak orientation of its accelerometer waveform segment is used to determine whether the flick is a flick up (initial peak is positive) or a flick down (initial peak is negative). Processor 515 then sends appropriate commands to Controller 452 to adjust the stimulation intensity accordingly. If a user wishes to stop an on-going therapy session, the user can simply tap the TENS device. Once the single tap is recognized under Active mode, Processor 515 sends a stop command to Controller 452 to stop further stimulation. The TENS device is then returned to its Standby mode.

On-skin detection module 265 also monitors the interface between electrode array 300 and the user's skin when the TENS device is in its Active mode by calculating the body resistor 208 (or more generally, the electrode-skin interface impedance). When the resistor value increases significantly (e.g., doubling its initial value), the quality of the electrode-skin interface is considered to have degraded significantly. The on-skin detection module 265 then sends a signal to Controller 452 to stop electrical stimulation so as to avoid an uncomfortable stimulation sensation due to a reduced electrode-skin contact area. Stopping electrical stimulation will also transition the TENS device from its Active mode to its Standby mode.

In another preferred form of the invention, instead of waiting for a user gesture (e.g., a single tap) to start a therapy session after TENS device 100 is placed on skin, the TENS device can automatically initiate a therapy session upon the device on-skin status changing to "true". It is reasonable to assume that if a user places the TENS device on their body, the user is seeking pain relief. This intuitive assumption can be leveraged to automatically initiate therapeutic stimulation. More specifically, and in one specific form of the present invention, upon placement of the TENS device on the upper calf of a user, the device automatically initiates stimulation 20 seconds after the on-skin condition is set to true. Similarly, removal of the TENS device from the body of the user suggests that the user no longer needs pain relief at that time and therefore the TENS device can automatically enter PowerSave mode without waiting for five minutes in Standby mode before entering the PowerSave mode, whereby to further optimize battery life.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. Apparatus for delivering transcutaneous electrical stimulation to a user, said apparatus comprising:
a housing;
a stimulator for electrically stimulating the user;
a monitor for monitoring motion of said housing; and
a controller for automatically transitioning at least one of said stimulator and said monitor between a standby mode and a power save mode;
wherein said power save mode supports a subset of the functionality of said stimulator and said monitor which is available in said standby mode so as to conserve battery power in said power save mode.

2. The apparatus according to claim 1 wherein said monitor uses at least one accelerometer mechanically coupled to said housing to monitor motion of said housing.

3. The apparatus according to claim 2 wherein said at least one accelerometer provides an acceleration signal associated with acceleration along at least one axis of three dimensional space.

4. The apparatus according to claim 1 wherein said controller transitions at least one of said stimulator and said monitor from said power save mode to said standby mode immediately upon detection of motion of said housing.

5. The apparatus according to claim 1 wherein said controller transitions at least one of said stimulator and said monitor from said standby mode to said power save mode if no motion of said housing is detected for a predetermined period of time.

6. The apparatus according to claim 1 wherein said stimulator is disconnected from a power supply when said stimulator is in said power save mode.

7. The apparatus according to claim 1 wherein said monitor samples accelerometer measurements at 50 Hertz when said monitor is in said power save mode.

8. The apparatus according to claim 1 wherein said stimulator is connected to a power supply when said stimulator is in said standby mode.

9. The apparatus according to claim 1 wherein said monitor samples accelerometer measurements at 100 Hertz when said monitor is in said standby mode.

10. The apparatus according to claim 1 wherein said monitor is programmed to determine one or more user gestures on said housing, in addition to determining motion of said housing, when said stimulator is in said standby mode.

11. The apparatus for delivering transcutaneous electrical stimulation to a user, said apparatus comprising:
a housing;
a stimulator for electrically stimulating the user;
a monitor for monitoring motion of said housing;
a remote-controller for indicating the proximity of a hand to said monitor; and
a controller for automatically modifying operation of said stimulator in response to the motion of the housing and proximity indication from the remote-controller.

12. The apparatus according to claim 11 wherein said monitor uses at least one accelerometer mechanically coupled to said housing in order to monitor motion of said housing.

13. The apparatus according to claim 12 wherein said accelerometer provides an acceleration signal associated with acceleration along at least one axis of three dimensional space.

14. The apparatus according to claim 11 wherein said remote-controller is a near-field communication device.

15. The apparatus according to claim 14 wherein said near-field communication device is a radio-frequency identification tag embedded in a ring on a user's finger.

16. The apparatus according to claim 11 wherein said proximity of a user's hand is registered when the hand interacts with said housing with a hand gesture, and further wherein said hand gesture comprises one selected from the group consisting of a tap, a slap, and a flick.

17. The apparatus according to claim 11 wherein said monitor calculates the likelihood that a waveform segment from the monitor is caused by transient activities not related to an intentional user gesture.

18. The apparatus according to claim 11 wherein said monitor calculates the likelihood that a waveform segment from the monitor is caused by an intentional user gesture.

19. The apparatus according to claim 11 wherein said monitor determines whether motion monitored by said monitor is an intentional user gesture by comparing the likelihood of a transient activity and the likelihood of an intentional user gesture.

20. The apparatus according to claim 18 wherein said likelihood is modified by the proximity indication from said remote-controller.

21. The apparatus according to claim 20 wherein said modification is to increase said likelihood.

22. A method for controlling transcutaneous electrical stimulation without mechanical actuators or buttons, said method comprising the steps of:
providing an apparatus for transcutaneous electrical stimulation in a user, said apparatus comprising:
a housing;
a stimulator for electrically stimulating the user;
a monitor for monitoring motion of said housing; and
a controller for automatically transitioning at least one of said stimulator and said monitor between a standby mode and a power save mode;
wherein said power save mode supports a subset of the functionality of said stimulator and said monitor which is available in said standby mode so as to conserve battery power in said power save mode;
determining presence of motion based on measurements from said monitor; and
transitioning at least one of said stimulator and said monitor between said standby mode and said power save mode.

23. The method according to claim 22 wherein said monitor uses at least one accelerometer mechanically coupled to said housing to monitor motion.

24. The method according to claim 22 wherein said controller transitions at least one of said stimulator and said monitor from said standby mode to said power save mode if no motion is detected for a predetermined period of time.

25. The method according to claim 22 wherein said controller transitions at least one of said stimulator and said monitor from said power save mode to said standby mode immediately upon detection of motion of said housing.

26. A method for controlling transcutaneous electrical stimulation without mechanical actuators or buttons, said method comprising the steps of:
providing an apparatus for transcutaneous electrical stimulation in a user, said apparatus comprising:
a housing;
a stimulator for electrically stimulating the user;
a monitor for monitoring motion of said housing;
a remote-controller for indicating the proximity of a hand to said monitor; and
a controller for automatically modifying operation of said stimulator in response to the motion of the housing and proximity indication from the remote-controller;
determining the presence of an intentional hand gesture based on measurements from said monitor and proximity indication from said remote-controller; and
controlling operation of said stimulator based on said intentional hand gesture.

27. The method according to claim 26 wherein said monitor uses at least one accelerometer mechanically coupled to said housing to monitor said motion.

28. The method according to claim 26 wherein said remote-controller is a near-field communication device, and further wherein the near-field communication device is a ring on the user's finger comprising a radio-frequency identification tag.

29. The method according to claim 26 wherein the proximity of the user's hand is registered when the hand interacts with said housing with a hand gesture.

30. The method according to claim 26 wherein said monitor analyzes said motion by calculating the likelihood that a waveform segment from the monitor is caused by transient activities not related to the intentional user gesture.

31. The method according to claim 26 wherein said monitor analyzes said motion by calculating the likelihood that a waveform segment from the monitor is caused by intentional user gesture.

32. The method according to claim 26 wherein said monitor determines whether motion monitored by the monitor is an intentional user gesture by comparing the likelihood of transient activity and the likelihood of an intentional user gesture.

33. The method according to claim 31 wherein said likelihood is modified by the proximity indication from said remote-controller.

34. The method according to claim 33 wherein said modification is to increase said likelihood.

\* \* \* \* \*